United States Patent
McGranahan et al.

(10) Patent No.: US 11,098,121 B2
(45) Date of Patent: Aug. 24, 2021

(54) "IMMUNE CHECKPOINT INTERVENTION" IN CANCER

(71) Applicant: CANCER RESEARCH TECHNOLOGY LIMITED, London (GB)

(72) Inventors: Nicholas McGranahan, London (GB); Rachel Rosenthal, London (GB); Charles Swanton, London (GB); Karl Peggs, London (GB); Sergio Quezada, London (GB)

(73) Assignee: CANCER RESEARCH TECHNOLOGY LIMITED, London (GB)

(*) Notice: Subject to any disclaimer, the term of this patent is extended or adjusted under 35 U.S.C. 154(b) by 275 days.

(21) Appl. No.: 15/758,165

(22) PCT Filed: Sep. 12, 2016

(86) PCT No.: PCT/EP2016/071471
§ 371 (c)(1),
(2) Date: Mar. 7, 2018

(87) PCT Pub. No.: WO2017/042394
PCT Pub. Date: Mar. 16, 2017

(65) Prior Publication Data
US 2018/0251553 A1   Sep. 6, 2018

(30) Foreign Application Priority Data
Sep. 10, 2015 (GB) ........................... 1516047

(51) Int. Cl.
| | | |
|---|---|---|
| A61K 39/395 | (2006.01) | |
| G16B 30/00 | (2019.01) | |
| C07K 16/28 | (2006.01) | |
| G16B 40/00 | (2019.01) | |
| G01N 33/574 | (2006.01) | |

(52) U.S. Cl.
CPC ....... C07K 16/2818 (2013.01); G01N 33/574 (2013.01); G01N 33/57411 (2013.01); G16B 30/00 (2019.02); G16B 40/00 (2019.02); *C07K 2317/24* (2013.01); *C07K 2317/76* (2013.01)

(58) Field of Classification Search
CPC ............ C07K 16/2818; C07K 2317/24; C07K 2317/76; G01N 33/57411; G01N 33/574; G16B 30/00; G16B 40/00
See application file for complete search history.

(56) References Cited

U.S. PATENT DOCUMENTS

| | | | |
|---|---|---|---|
| 5,670,325 A * | 9/1997 | Lapidus | C12Q 1/6809 435/6.12 |
| 10,023,635 B2 | 7/2018 | Sazinsky et al. | |
| 10,426,824 B1 | 10/2019 | Hacohen et al. | |
| 2014/0120622 A1 | 5/2014 | Gregory et al. | |
| 2015/0125477 A1 | 5/2015 | Kuttruff-Coqui et al. | |
| 2016/0101170 A1 | 4/2016 | Hacohen et al. | |
| 2016/0339090 A1 | 11/2016 | Hacohen et al. | |
| 2017/0016075 A1 | 1/2017 | Velculescu et al. | |
| 2018/0000851 A1 | 1/2018 | Krieg | |
| 2018/0064793 A1 | 3/2018 | Mcgranahan et al. | |
| 2019/0002590 A1 | 1/2019 | Bradley et al. | |
| 2019/0023787 A1 * | 1/2019 | Diaz | A61P 1/04 |
| 2019/0388400 A1 | 12/2019 | Christiano | |
| 2020/0000903 A1 | 1/2020 | McGranahan et al. | |
| 2020/0000904 A1 | 1/2020 | McGranahan et al. | |
| 2020/0316183 A1 | 10/2020 | Weinschenk et al. | |

FOREIGN PATENT DOCUMENTS

| | | |
|---|---|---|
| EP | 1762575 A1 | 3/2007 |
| JP | 2016-531116 A | 10/2016 |
| WO | WO-88/00344 A1 | 1/1988 |
| WO | WO-2010/060439 A1 | 6/2010 |
| WO | WO-2010/144192 A1 | 12/2010 |
| WO | WO-2011/014356 A1 | 2/2011 |
| WO | WO-2011/041613 A2 | 4/2011 |
| WO | WO-2011/143656 A2 | 11/2011 |
| WO | WO-2012/159643 A1 | 11/2012 |
| WO | WO-2012/159754 A2 | 11/2012 |
| WO | WO-2014/012051 A1 | 1/2014 |
| WO | WO-2014/026096 A1 | 2/2014 |
| WO | WO-2014/055561 A1 | 4/2014 |
| WO | WO-2014/168874 A2 | 10/2014 |
| WO | WO-2015/014375 A1 | 2/2015 |
| WO | WO-2015/014869 A1 | 2/2015 |
| WO | WO-2015/085233 A1 | 6/2015 |
| WO | WO-2015/095811 A2 | 6/2015 |
| WO | WO-2015/103037 A2 | 7/2015 |
| WO | WO-2016/077553 A1 | 5/2016 |

(Continued)

OTHER PUBLICATIONS

Yap et al, Sci Transl Med, 28:127ps10, 2012.*
Van Rooij et al., Tumor exome analysis reveals neoantigen-specific T-cell reactivity in an ipilimumab-responsive melanoma, J Clin Oncol., 31(32):e439-e442 (2013).
Akarca et al., BRAF V600E mutation-specific antibody, a sensitive diagnostic marker revealing minimal residual disease in hairy cell leukaemia, Br. J. Haematol., 162(6):848-51 (2013).
Andersen et al., Parallel detection of antigen-specific T cell responses by combinatorial encoding of MHC multimers, Nat. Protoc., 7(5):891-902 (2012).
Ares, Methods for processing high-throughput RNA sequencing data, Cold Spring Harb. Protoc., 2014(11):1139-48 (2014).

(Continued)

*Primary Examiner* — Mark Halvorson
(74) *Attorney, Agent, or Firm* — Marshall, Gerstein & Borun LLP

(57) ABSTRACT

The present invention relates to methods for identifying a subject with cancer who is suitable for treatment with an immune checkpoint intervention, and to methods of treatment of such subjects. The invention further relates to a method for predicting or determining the prognosis of a subject with cancer.

25 Claims, 29 Drawing Sheets
(25 of 29 Drawing Sheet(s) Filed in Color)
Specification includes a Sequence Listing.

(56) References Cited

FOREIGN PATENT DOCUMENTS

| WO | WO-2016/081947 A2 | 5/2016 |
|---|---|---|
| WO | WO-2016/145578 A1 | 9/2016 |
| WO | WO-2016/146035 A1 | 9/2016 |
| WO | WO-2016/174085 A1 | 11/2016 |
| WO | WO-2017/042394 A1 | 3/2017 |

OTHER PUBLICATIONS

Bakker et al., Conditional MHC class I ligands and peptide exchange technology for the human MHC gene products HLA-A1, -A3, -A11, and -B7, Proc. Natl. Acad. Sci. USA, 105(10:3825-30(2008).
Bao et al., Review of current methods, applications, and data management for the bioinformatics analysis of whole exome sequencing, Cancer Inform., 13(Suppl 2):67-82 (2014).
Chang et al., Conditional ligands for Asian HLA variants facilitate the definition of CD8+ T-cell responses in acute and chronic viral diseases, Eur. J. Immunol., 43(4):1109-20 (2013).
De Bruin et al., Spatial and temporal diversity in genomic instability processes defines lung cancer evolution, Science, 346(6206):251-6 (2014).
Frøsig et al., Design and validation of conditional ligands for HLA-B*08:01, HLA-B*15:01, HLA-B*35:01, and HLA-B*44:05, Cytometry A, 87(10):967-75 (2015).
Gerlinger et al., Genomic architecture and evolution of clear cell renal cell carcinomas defined by multiregion sequencing, Nat. Genet., 46(3):225-33 (2014).
Gerlinger et al., Intratumor heterogeneity and branched evolution revealed by multiregion sequencing, N. Engl. J. Med., 366(10):883-92 (2012).
Hadrup et al., Parallel detection of antigen-specific T-cell responses by multidimensional encoding of MHC multimers, Nat. Methods, 6(7):520-6 (2009).
Hodgkinson et al., Tumorigenicity and genetic profiling of circulating tumor cells in small-cell lung cancer, Nat. Med., 20(8):897-903 (2014).
Hoof et al., NetMHCpan, a method for MHC class I binding prediction beyond humans, Immunogenetics, 61(1):1-13 (2009).
International Application No. PCT/EP2016/071471, International Preliminary Report on Patentability, dated Jan. 12, 2018.
International Application No. PCT/EP2016/071471, International Search Report and Written Opinion, dated Dec. 20, 2016.
International Application No. PCT/EP2016/071471, Written Opinion of the International Preliminary Examining Authority, dated Aug. 11, 2017.
Kammermeier et al., Targeted gene panel sequencing in children with very early onset inflammatory bowel disease—evaluation and prospective analysis, J. Med. Genet., 51(11):748-55 (2014).
Koboldt et al., VarScan 2: somatic mutation and copy number alteration discovery in cancer by exome sequencing, Genome Res., 22(3):568-76 (2012).
Landau et al., Evolution and impact of subclonal mutations in chronic lymphocytic leukemia, Cell, 152(4):714-26 (2013).
Lawrence et al., Discovery and saturation analysis of cancer genes across 21 tumour types, Nature, 505(7484):495-501 (2014).
Li et al., Fast and accurate short read alignment with Burrows-Wheeler transform, Bioinformatics, 25(14):1754-60 (2009).
Li et al., The Sequence Alignment/Map format and SAMtools, Bioinformatics, 25(16):2078-9 (2009).
Marafioti et al., Novel markers of normal and neoplastic human plasmacytoid dendritic cells, Blood, 111(7):3778-92 (2008).
Marafioti et al., Phenotype and genotype of interfollicular large B cells, a subpopulation of lymphocytes often with dendritic morphology, Blood, 102(8):2868-76 (2003).
Mardis, Next-generation sequencing platforms, Annu. Rev. Anal. Chem., 6:287-303 (2013).
McGranahan et al., Clonal neoantigens elicit T cell immunoreactivity and sensitivity to immune checkpoint blockade, Science, 351(6280):1463-9 (2016).
McGranahan et al., Clonal status of actionable driver events and the timing of mutational processes in cancer evolution, Sci. Transl. Med., 7(283):283ra54 (2015).
McKenna et al., The Genome Analysis Toolkit: a MapReduce framework for analyzing next-generation DNA sequencing data, Genome Res., 20(9):1297-303 (2010).
Meyerson et al., Advances in understanding cancer genomes through second-generation sequencing, Nat. Rev. Genet., 11(10):685-96 (2010).
Murugaesu et al., Tracking the genomic evolution of esophageal adenocarcinoma through neoadjuvant chemotherapy, Cancer Discov., 5(8):821-31 (2015).
Nakamura et al., Sequence-specific error profile of Illumina sequencers, Nucleic Acids Res., 39(13):e90 (2011).
Nielsen et al., NetMHCpan, a method for quantitative predictions of peptide binding to any HLA-A and -B locus protein of known sequence, PLoS One, 2(8):e796 (2007).
Perkel, Build your own gene panels with these custom NGS targeting tools, Biocompare (The Buyer's Guide for Life Scientists) (May 8, 2014).
Rizvi et al., Cancer immunology. Mutational landscape determines sensitivity to PD-1 blockade in non-small cell lung cancer, Science, 348(6230):124-8 (2015).
Robinson et al., Integrative genomics viewer, Nat. Biotechnol., 29(1):24-6 (2011).
Shukla et al., Comprehensive analysis of cancer-associated somatic mutations in class I HLA genes, Nat. Biotechnol., 33(11):1152-8 (2015).
Szolek et al., OptiType: precision HLA typing from next-generation sequencing data, Bioinformatics, 30(23):3310-6 (2014).
Toebes et al., Design and use of conditional MHC class I ligands, Nat. Med., 12(2):246-51 (2006).
Wang et al., ANNOVAR: functional annotation of genetic variants from high-throughput sequencing data, Nucleic Acids Res., 38(16):e164 (2010).
Yap et al., Whole-exome sequencing of muscle-invasive bladder cancer identifies recurrent mutations of UNC5C and prognostic importance of DNA repair gene mutations on survival, Clin. Cancer Res., 20(24):6605-17 (2014).
Bodansky, Peptide Chemistry, A Practical Textbook, Springer-Verlag, Berlin (1988).
Butterfield, Cancer vaccines, BMJ, 350:h988 (2015).
Clackson et al., Making antibody fragments using phage display libraries, Nature, 352(6336):624-8 (Aug. 1991).
Creighton, Proteins Structures and Molecular Principles, WH Freeman and Co, New York NY (1983).
Donia et al., Characterization and comparison of 'standard' and 'young' tumour-infiltrating lymphocytes for adoptive cell therapy at a Danish translational research institution, Scand. J. Immunol., 75(2):157-67 (2012).
Donia et al., Simplified protocol for clinical-grade tumor-infiltrating lymphocyte manufacturing with use of the Wave bioreactor, Cytotherapy, 16(8):1117-20 (2014).
Dudley et al., CD8+ enriched "young" tumor infiltrating lymphocytes can mediate regression of metastatic melanoma, Clin. Cancer Res., 16(24):6122-31 (2010).
Dudley et al., Generation of tumor-infiltrating lymphocyte cultures for use in adoptive transfer therapy for melanoma patients, J. Immunother., 26(4):332-42 (2003).
Forget et al., Activation and propagation of tumor-infiltrating lymphocytes on clinical-grade designer artificial antigen-presenting cells for adoptive immunotherapy of melanoma, J. Immunother., 37(9):448-60 (2014).
Gerlinger et al., Ultra-deep T cell receptor sequencing reveals the complexity and intratumour heterogeneity of T cell clones in renal cell carcinomas, J. Pathol., 231(4):424-32 (2013).
Gillies et al., Evolutionary dynamics of carcinogenesis and why targeted therapy does not work, Nat. Rev. Cancer, 12(7):487-93 (2012).
Hartmann et al., Dermatopathology, SEREX identification of new tumour-associated antigens in cutaneous T-cell lymphoma, Br. J. Dermatol., 150(2):252-8 (2004).

(56) References Cited

OTHER PUBLICATIONS

International Application No. PCT/EP2016/059401, International Preliminary Report on Patentability, dated Oct. 31, 2017.
International Application No. PCT/EP2016/059401, International Search Report and Written Opinion, dated Jul. 1, 2016.
Jamal-Hanjani et al., Tracking genomic cancer evolution for precision medicine: the lung TRACERx study, PLoS Biol., 12(7):e1001906 (2014).
Jamal-Hanjani et al., Translational implications of tumor heterogeneity, Clin. Cancer Res., 21(6):1258-66 (2015).
Jamal-Hanjani et al., Tumour heterogeneity and immune-modulation, Curr. Opin. Pharmacol., 13(4):497-503 (2013).
Köhler et al., Continuous cultures of fused cells secreting antibody of predefined specificity, Nature, 256(5517):495-7 (1975).
Lundegaard et al., Accurate approximation method for prediction of class I MHC affinities for peptides of length 8, 10 and 11 using prediction tools trained on 9mers, Bioinformatics, 24(11):1397-8 (2008).
Lundegaard et al., NetMHC-3.0: accurate web accessible predictions of human, mouse and monkey MHC class I affinities for peptides of length 8-11, Nucleic Acids Res., 36(Web Server Issue):W509-12 (2008).
Marks et al., By-passing immunization. Human antibodies from V-gene libraries displayed on phage, J. Mol. Biol., 222(3):581-97 (Dec. 1991).
Obenaus et al., Identification of human T-cell receptors with optimal affinity to cancer antigens using antigen-negative humanized mice, Nat. Biotechnol., 33(4):402-7 (2015).
Rajasagi et al., Systematic identification of personal tumor-specific neoantigens in chronic lymphocytic leukemia, Blood, 124(3):453-62 (2014).
Roberge et al., A strategy for a convergent synthesis of N-linked glycopeptides on a solid support, Science, 269(5221):202-4 (1995).
Rooney et al., Infusion of cytotoxic T cells for the prevention and treatment of Epstein-Barr virus-induced lymphoma in allogeneic transplant recipients, Blood, 92(5):1549-55 (1998).
Rosenberg et al., Durable complete responses in heavily pretreated patients with metastatic melanoma using T-cell transfer immunotherapy, Clin. Cancer Res., 17(13):4550-7 (2011).
Shen et al., An effective and effecient peptide binding prediction approach for a broad set of HLA-DR molecules based on ordered weighted averaging of binding pocket profiles, Proteome Sci., 11(Suppl 1):S15 (2013).
Trapnell et al., TopHat: discovering splice junctions with RNA-Seq, Bioinformatics, 25(9):1105-11 (2009).
Trapnell et al., Transcript assembly and quantification by RNA-Seq reveals unannotated transcripts and isoform switching during cell differentiation, Nat. Biotechnol., 28(5):511-5 (2010).
Weese et al., RazerS 3: faster, fully sensitive read mapping, Bioinformatics, 28(20):2592-9 (2012).
Ye et al., Engineered artificial antigen presenting cells facilitate direct and efficient expansion of tumor infiltrating lymphocytes, J. Transl. Med., 9:131 (2011).
Takeuchi et al., PD-1 inhibitor nivolumab—from bench to bedside, Igaku-no-Ayumi [in Japanese], Journal of Clinical and Experimental Medicine, Aug. 29, 2015, vol. 254, No. 9, pp. 777-783.
Taube et al., Association of PD-1, PD-1 ligands, and other features of the tumor immune microenvironment with response to anti-PD-1 therapy, Clinical Cancer Research, Oct. 1, 2014 (Epub Apr. 8, 2014), vol. 20, No. 19, pp. 5064-5074.
Topalian et al., Safety, activity, and immune correlates of anti-PD-1 antibody in cancer, N Engl J Med., Jun. 28, 2012 (Epub Jun. 2, 2012), vol. 366, No. 26, pp. 2443-2454.
Japanese Patent Application No. 2018-512548, Notice of Reasons for Rejection, dated Apr. 7, 2020.
Birkeland et al., Patterns of genomic evolution in advanced melanoma, Nat. Commun., 9(1):2665 (Jul. 2018).
Blankenstein et al., Targeting cancer-specific mutations by T cell receptor gene therapy, Curr. Opin. Immunol., 33:112-9 (Apr. 2015).

Carreno et al., Abstract LB-237: Vaccination increases the breadth and diversity of melanoma neoantigen-specific T cells in humans, Proceedings: AACR 106th Annual Meeting 2015, Philadelphia, PA, Cancer Res., 75(15 Suppl):Abstract nr LB-237 (Apr. 2015).
Chin et al., Immune intervention with monoclonal antibodies targeting CD152 (CTLA-4) for autoimmune and malignant diseases, Chang Gung Med. J., 31(1):1-15 (Jan.-Feb. 2008).
El-Sayes et al., Tumor heterogeneity: A great barrier in the agent of cancer immunotherapy, Cancers, 13:806 (2021).
European Patent Application No. 16718705.3, Examination Report, dated Nov. 5, 2018.
Hacochen et al., Getting personal with neoantigen-based therapeutic cancer vaccines, Cancer Immunol. Res., 1(1):11-15 (2013).
Hinrichs et al., Exploiting the curative potential of adoptive T-cell therapy for cancer, Immunol. Rev., 257(1):56-71 (Jan. 2014).
Jamal-Hanjani et al., Tracking the evolution of non-small-cell lung cancer, N. Engl. J. Med., 376(22):2109-2121 (Jun. 2017).
Japanese Patent Application No. 2018-512548, Search Report, dated Mar. 11, 2020.
Jiang et al., A novel peptide isolated from a phage display peptide library with trastuzumab can mimic antigen epitope of HER-2, J. Biol. Chem., 280(6):4656-62 (Feb. 2005).
Li et al., Cancer genome sequencing and its implications for personalized cancer vaccines, Cancers (Basel), 3(4):4191-211 (2011).
Loeb et al., Extensive subclonal mutational diversity in human colorectal cancer and its significance, Proc. Natl. Acad. Sci. USA, 116(52):26863-72 (Dec. 2019).
Lu et al., Efficient identification of mutated cancer antigens recognized by T cells associated with durable tumor regressions, Clin. Cancer Res., 20(13):3401-10 (Jul. 2014).
Lu et al., Mutated PPP1R3B is recognized by T cells used to treat a melanoma patient who experienced a durable complete tumor regression, J. Immunol., 190(12):6034-42 (Jun. 2013).
Nowell, The clonal evolution of tumor cell populations, Science, 194(4260):23-8 (Oct. 1976).
Palucka et al., Dendritic-cell-based therapeutic cancer vaccines, Immunity, 39:38-48 (Jul. 2013).
Pardoll et al., The role of CD4+ T cell responses in antitumor immunity, Curr. Opin. Immunol., 10(5):588-94 (Oct. 1998).
Pardoll, T cells take aim at cancer, PNAS, 99(25):18540-2 (Dec. 2002).
Riemer et al., Matching of trastuzumab (Herceptin) epitope mimics onto the surface of Her-2/neu—a new method of epitope definition, Mol. Immunol., 42(9):1121-4 (May 2005).
Robbins et al., Mining exomic sequencing data to identify mutated antigens recognized by adoptively transferred tumor-reactive T cells, Nat. Med., 19(6):747-52 (Jun. 2013).
Schumacher et al., A vaccine targeting mutant IDH1 induces antitumour immunity, Nature, 512(7514):324-7 (Aug. 2014).
Schumacher et al., Neoantigens in cancer immunotherapy, Science, 348(6230):69-74 (Apr. 2015).
Slingluff et al., Melanomas with concordant loss of multiple melanocytic differentiation proteins: immune escape that may be overcome by targeting unique or undefined antigens, Cancer Immunol. Immunother., 48(12):661-72 (Mar. 2000).
Topalian et al., Expansion of human tumor infiltrating lymphocytes for use in immunotherapy trials, J. Immunol. Methods, 102(1):127-41 (Aug. 1987).
Turajlic et al., Tracking cancer evolution reveals constrained routes to metastases: TRACERx Renal, Cell, 173:581-594 (2018).
Von Loga et al., Extreme intratumour heterogeneity and driver evolution in mismatch repair deficient gastro-oesophageal cancer, Nat. Commun., 11(1):139 (Jan. 2020).
Wu et al., Adoptive T-cell therapy using autologous tumor-infiltrating lymphocytes for metastatic melanoma: current status and future outlook, Cancer J., 18(2):160-75 (Mar.-Apr. 2012).
Yates et al., Subclonal diversification of primary breast cancer revealed by multiregion sequencing, Nat. Medicine, 21(7):731-44 (Jul. 2015).

\* cited by examiner

● clonal putative neoantigens (<500nM)
● subclonal putative neoantigens (<500nM)

Figure 7B
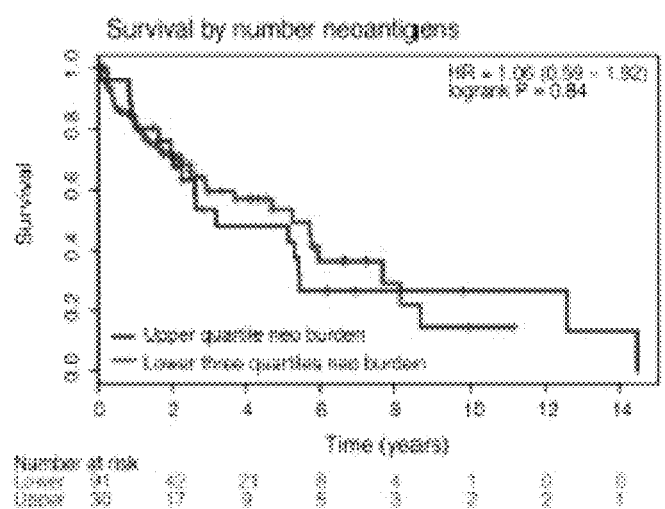
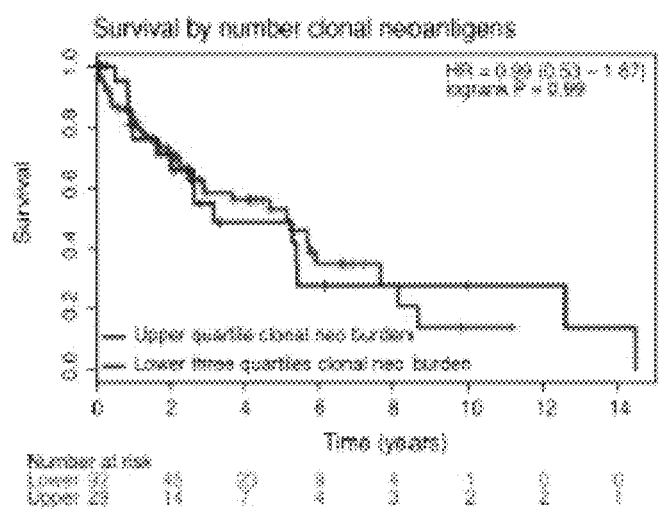
Figure 7C

"IMMUNE CHECKPOINT INTERVENTION" IN CANCER

CROSS-REFERENCE TO RELATED APPLICATIONS

This application is the U.S. National Phase of International Application No. PCT/EP2016/071471, filed Sep. 12, 2016, which claims priority to Application No. 1516047.6, filed on Sep. 10, 2015, in the United Kingdom.

INCORPORATION BY REFERENCE OF MATERIAL SUBMITTED ELECTRONICALLY

This application incorporates by reference in its entirety a computer-readable nucleotide/amino acid sequence listing identified as one 3,171 bytes ASCII (text) file named "51379_SeqListing.txt," created Jan. 31, 2018.

FIELD OF THE INVENTION

The present invention relates to methods for identifying a subject with cancer who is suitable for treatment with an immune checkpoint intervention, and to methods of treatment of such subjects. The invention further relates to a method for predicting or determining the prognosis of a subject with cancer.

BACKGROUND TO THE INVENTION

Among the most promising approaches to activating therapeutic antitumour immunity is the blockade of immune checkpoints. Immune checkpoints are inhibitory pathways in the immune system that are crucial for maintaining self-tolerance and modulating the duration and amplitude of physiological immune responses in peripheral tissues in order to minimize collateral tissue damage. It is now clear that tumours co-opt certain immune-checkpoint pathways as a major mechanism of immune resistance, particularly against T cells that are specific for tumour antigens. Because many of the immune checkpoints are initiated by ligand-receptor interactions, they can be readily blocked by antibodies or modulated by recombinant forms of ligands or receptors.

Current approaches to immune checkpoint regulation in cancers involve a level of guesswork and serendipity based mostly in the order these compounds have been made available. CTLA4, PD-1 and PDL1 were discovered and produced in this order, and that is how they have been administered so far. Initial trials were carried out with CTLA-4, as this was the first to be approved by the FDA. Subsequently, PD-1/PDL1 treatments were approved and used.

WO 2015/103037 provides a method for identifying a subject as likely to respond to treatment with an immune checkpoint modulator, based on the discovery that cancer cells may harbour somatic mutations that result in neoepitopes that are recognisable by a patient's immune system as non-self. The identification of one or more neoepitopes in a cancer sample may be useful for determining which cancer patients are likely to respond favourably to treatment with an immune checkpoint modulator.

SUMMARY OF THE INVENTION

The present inventors have made the important and surprising determination that cancer patients with higher numbers of clonal neo-antigens, and/or a higher ratio of clonal:sub-clonal neoantigens or a low sub-clonal neo-antigen fraction, are more likely to respond to treatment with an immune checkpoint internvention.

As demonstrated in the present examples, patients with tumours with a high clonal neo-antigen burden and/or a low subclonal neo-antigen burden have a better response to immunotherapy with checkpoint blockade (e.g. anti-PD1 therapy). This represents an important contribution to the art, in that it opens up the potential for improved and more directed treatments and preventative modalities for treating and preventing cancer. In this regard, therapeutic and preventative interventions can be targeted to the individual and to the particular context of the cancer.

Furthermore, the present inventors have found that, surprisingly, tumour cells with high numbers of clonal neo-antigens exhibit similar expression profiles of immune checkpoint molecules, that is they exhibit a common expression profile of immune checkpoint molecules. This is an important contribution to the art, as it has not previously been demonstrated that cancers of specific types exhibit particular expression profiles of immune checkpoint molecules. The present inventors have shown this for the first time, and this finding facilitates more directed approaches to treating or preventing particular cancers.

The present inventors have also surprisingly found that patients with higher numbers of clonal mutations, and a higher ratio of clonal:sub-clonal mutations, have improved prognosis.

The present invention therefore addresses a need in the art for new, alternative and/or more effective ways of treating and preventing cancer.

Accordingly, the present invention provides a method for identifying a subject with cancer who is suitable for treatment with an immune checkpoint intervention, said method comprising:
  (i) determining the number of clonal neo-antigens in one or more cancer cells from said subject; and/or
  (ii) determining the ratio of clonal:sub-clonal neo-antigens and/or sub-clonal neo-antigen fraction in more than one cancer cell from said subject; and/or
  (iii) determining the expression profile of immune checkpoint molecules in cancer cells and/or tumour infiltrating immune cells from said subject, or tumour type, wherein a higher number of clonal neo-antigens, and/or a higher ratio of clonal:sub-clonal neo-antigens, or lower (or low) sub-clonal neo-antigen fraction, and/or differential immune checkpoint molecule expression in comparison to a reference sample is indicative of response to an immune checkpoint intervention.

In another aspect, the invention provides a method for predicting or determining the prognosis of a subject with cancer, the method comprising:
  (i) determining the number of clonal neo-antigens in one or more cancer cells from said subject; and/or
  (ii) determining the ratio of clonal:sub-clonal neo-antigens and/or sub-clonal neo-antigen fraction in more than one cancer cell from said subject,
wherein a higher number of clonal neo-antigens and/or a higher ratio of clonal:sub-clonal neo-antigens, or lower (or low) sub-clonal neo-antigen fraction, is indicative of improved prognosis.

In a further aspect, the invention provides a method of treating or preventing cancer in a subject, wherein said method comprises the following steps:

i) identifying a subject with cancer who is suitable for treatment with an immune checkpoint intervention according to the method of the invention; and ii) treating said subject with an immune checkpoint intervention.

In a yet further aspect, the invention provides a method of treating or preventing cancer in a subject which comprises treating a subject with cancer with an immune checkpoint intervention, wherein the subject has been determined to have (i) a higher number of clonal neo-antigens; and/or (ii) a higher ratio of clonal:sub-clonal neo-antigens, or lower (or low) sub-clonal neo-antigen fraction; and/or (iii) a differential immune checkpoint molecule expression in comparison to a reference sample.

The invention also provides an immune checkpoint intervention for use in a method of treatment or prevention of cancer in a subject, the method comprising:

i) identifying a subject with cancer who is suitable for treatment with an immune checkpoint intervention according to the method of the invention; and ii) treating said subject with an immune checkpoint intervention.

The invention further provides an immune checkpoint intervention for use in the treatment or prevention of cancer in a subject, wherein the subject has (i) a higher number of clonal neo-antigens; and/or (ii) a higher ratio of clonal:sub-clonal neo-antigens, or lower (or low) sub-clonal neo-antigen fraction; and/or (iii) a differential immune checkpoint molecule expression in comparison to a reference sample.

DESCRIPTION OF THE FIGURES

This patent or application file contains at least one drawing executed in color. Copies of this patent or patent application publication with color drawing(s) will be provided by the United States Patent and Trademark Office upon request and payment of the necessary fee.

(FIG. 1A) Total putative neo-antigen burden in cohort of TOGA LUAD (LUng ADenocarcinoma) tumours. Proportion of neo-antigens arising from clonal (blue) or subclonal (red) mutations or those of undetermined (grey) clonality is shown. (FIG. 1B) Overall survival curves for patients with tumours exhibiting high neo-antigen burden, defined as the upper quartile of the cohort, (n=30) compared to remainder of cohort (n=86) (log-rank P=0.011), (FIG. 1C) high clonal neo-antigen burden, defined as the upper quartile of the cohort, (n=29) compared to remainder of cohort (n=87) (log-rank P=0.0077), and (FIG. 1D) high subclonal neo-antigen burden, defined as the upper quartile of the cohort (n=30) compared to remainder of cohort (n=86) (log-rank P=0.12). (FIG. 1E) Differentially expressed genes between the tumours with high clonal neo-antigen burden and low clonal neo-antigen burden, defined as the bottom quartile of the cohort, clustered on co-expression. Clusters of immune genes highlighted in the text are boxed.

FIG. 2A) Phylogenetic trees for L011 and L012, with trunk and branch lengths proportional to number of non-silent mutations. FIG. 2B) Putative neo-antigens predicted for all missense mutations in L011. The MTFR2D326Y neo-antigen (FAFQEYDSF) is highlighted. FIG. 2C) Putative neo-antigens predicted for all missense mutations in L012. The CHTF18 L769V neo-antigen (LLLDIVAPK) and MYADMR3OW neo-antigen (SPMIVGSPW) are indicated. FIG. 2D, FIG. 2E) MHC-multimer analysis of in vitro expanded CD8+T lymphocytes deriving from three tumour regions and normal tissues for L011 (FIG. 2D) and L012 (FIG. 2E). In both cases, frequency of CD3+CD8+T lymphocytes reactive to mutant peptides are indicated.

FIG. 3A) MHC-multimer analysis of non-expanded CD8+ T cells from tumour regions 1-3, adjacent normal lung tissue and PBMCs from patient L011 (upper panel) and L012 (lower panel). Frequency of MHC-multimer positive cells out of the CD3+CD8+ compartment is indicated. FIG. 3B) Immunophenotype of tumour-infiltrating CD8+ T cells from patient L011, comparing MTFR2-reactive CD8+ T cells (MTFR2+) with MHC-multimer negative CD8+ T cells (MTFR2-) in the same tumour region, in normal tissue and in PBMCs. Data shown is from tumour Region 3 and representative of all regions. Percentage of cells expressing CTLA-4, PD-1, LAG-3, Ki-67 and GzmB is shown. FIG. 3C) Co-expression of PD-1, Ki67 and GzmB on MTFR2-reactive (MTFR2+) and non-reactive CD8+ T cells (MTFR2-) FIG. 3D) Upper panel: Multi-color IHC of primary tumour from L011 and L012. CD8 (red), Granzyme B (blue) and LAG-3 (brown) are shown. Lower panel: PD-L1 staining in L011 region 3 versus adjacent normal tissue.

FIG. 4G) Clonal architecture for each sequenced tumour. PFS are reported under barplot and those with ongoing progression-free survival are labeled with +. PD-L1 is indicated below barplot: Strong (+) 50% membranous staining; Weak (+/−), 1-49% membranous staining; Negative (−),<1% membranous staining; Unknown (?). (FIG. 4H) Progression free survival in combined tumour cohort comparing tumours with a higher number of neo-antigens and low subclonal fraction with those with a lower number of neo-antigens or high subclonal fraction. FIG. 4I) Clonal architecture of CA9903 tumour sample, with HERC1 mutation highlighted and with subclones indicated. FIG. 4J) Putative neo-antigens predicted for all missense mutations in CA9903. The HERC1P3278S neo-antigen (ASNASSAAK) is highlighted.

(FIG. 6A) Overall survival curves of patients harboring tumours with high SNV burden (n=30) compared to remainder of cohort (n=86) (log-rank P=0.01), (FIG. 6B) high clonal SNV burden (n=30) compared to remainder of cohort (n=86) (log-rank P=0.014), and (FIG. 6C) high subclonal SNV burden (n=30) compared to remainder of cohort (n=86) (log-rank P=0.14).

FIGS. 7A-FIG. 7G: LUSC (Lung Squamous cell carcinoma) cohort summary. (FIG. 7A) Total putative neo-antigen burden of TOGA LUSCpatients. Columns coloured to show proportion of neo-antigens arising from clonal blue) or subclonal (red) mutations or arising from mutations of undetermined (grey) clonality. (FIG. 7B) Overall survival curves of patients with high neo-antigen burden (n=30) compared to those with a low neo-antigen burden (n=91) (log-rank P=0.84), (FIG. 7C) high clonal neo-antigen burden (n=29) compared to those with a low clonal neo-antigen burden (n=92) (log-rank P=0.99), and (FIG. 7D) high subclonal neo-antigen burden (n=30) compared to those with a low subclonal neo-antigen burden (n=91) (log-rank P=0.32). (FIG. 7E) Overall survival curves of patients with high SNV burden (n=30) compared to remainder of cohort (n=90) (log-rank P=0.52), (FIG. 7F) high clonal SNV burden (n=30) compared to remainder of cohort (n=91) (log-rank P=0.89), and (FIG. 7G) high subclonal SNV burden (n=30) compared to remainder of cohort (n=92) (log-rank P=0.28).

FIG. 9B) Co-expression of PD-1, Ki67 and granzyme B on tumour-infiltrating CD8+CHTF18-reactive (CHTF18+) and MYADM-reactive (MYADM+) T cells compared to tumour infiltrating MHC-multimer negative CD8+ T cells (Multimer-). FIG. 9C) In vitro expanded tumour-infiltrating CD8+ T cells were stained with MHC-multimers loaded with either mutant or wild type peptides and analyzed by flow cytometry. Percentage of MHC multimer positive cells of the CD3+CD8+ gate is shown. L011 (Top panel): Expanded CD8+ T cells from tumour region 1 recognize mutant but not wild type MTFR2. L012 (middle panel): Expanded CD8+ T cells from tumour region 2 recognize mutant but not wild type CHTF18. L012 (bottom panel): Expanded CD8+ T cells from tumour region 2 recognize both mutant and wild type MYADM. The mutation in MYADM is on the anchor residue, primary affecting HLA binding and not T cell recognition. Whilst the data suggest that T cells in this patient can recognize both mutant and wildtype peptides (when stabilized in our MHC-multimer system), the very low affinity of the wild type peptide would prevent adequate presentation in vivo. (FIG. 9D) Validation of BV650 and PE-Cy7 MHC-multimer binding to expanded tumour-infiltrating lymphocytes from L011 and L012. To validate the quality of the reagents used to characterize MTFR2-, MYADM- and CHTF18-reactive T cells in non-expanded tumour samples, we used the same reagents to stain a larger number of expanded TILs. Data from L011 (left panel), and L012 (right panel) show clear and defined populations of MTFR2-, MYADM- and CHTF18-reactive T cells in the expanded TILs.

FIG. 12A) Number of predicted clonal mutations in the discovery cohort tumours from patients with a durable clinical benefit (DCB) or with non durable benefit (NDB). FIG. 12B) Subclonal fraction in tumours from patients with a DCB or NDB FIG. 12C) Progression free survival in discovery tumours with a higher number of clonal mutations and low subclonal fraction compared to those with a lower number of clonal mutations or high subclonal fraction. FIG. 12D) Number of predicted clonal mutations in the validation cohort tumours from patients with a DCB or with NDB. FIG. 12E) Subclonal fraction in tumours from validation patients with a DCB or NDB FIG. 12F) Progression free survival in validation tumours with a higher number of clonal mutations and low subclonal fraction compared to those with a lower number of clonal mutations or high subclonal fraction. FIG. 12G) Number of clonal and subclonal mutations for each sequenced tumour with clonal (dark shading) and subclonal (light shading) displayed in the barplot. Bars are shaded to indicate clinical benefit status: DCB, green; NDB, red. PFS are reported under the barplot and those with ongoing progression-free survival are labelled with +. PD-L1 is indicated below barplot: Strong (+) 50% membraneous staining; Weak (+/−), 1-49% membraneous staining; Negative (−), 1% membraneous staining; Unknown (?), unassessable. FIG. 12H) Progression free survival in combined tumour cohort comparing tumours with a higher number of clonal mutations and low subclonal fraction with those with a lower number of clonal mutations or high subclonal fraction.

DETAILED DESCRIPTION OF THE INVENTION

Figure 1A:
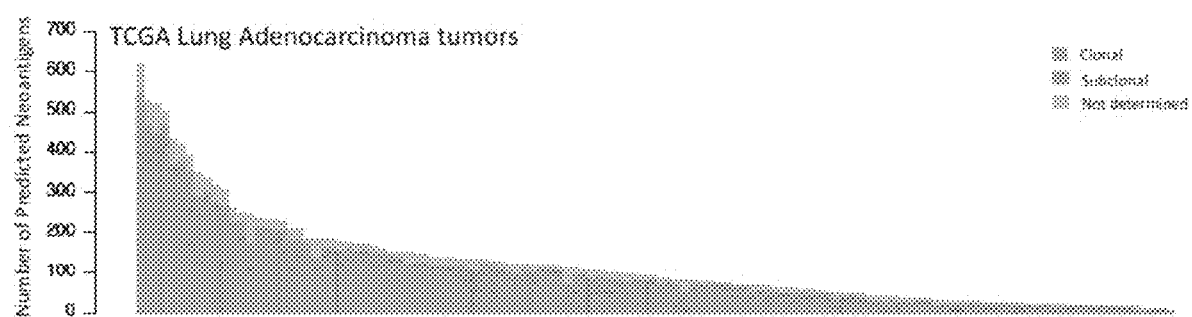
FIGS. 1A-FIG. 1E.

A "neo-antigen" is a tumour-specific antigen which arises as a consequence of a mutation within a cancer cell. Thus, a neo-antigen is not expressed by healthy cells in a subject.

The neo-antigen described herein may be caused by any non-silent mutation which alters a protein expressed by a cancer cell compared to the non-mutated protein expressed by a wild-type, healthy cell. For example, the mutated protein may be a translocation or fusion.

A "mutation" refers to a difference in a nucleotide sequence (e.g. DNA or RNA) in a tumour cell compared to a healthy cell from the same individual. The difference in the nucleotide sequence can result in the expression of a protein which is not expressed by a healthy cell from the same individual.

For example, the mutation may be a single nucleotide variant (SNV), multiple nucleotide variants, a deletion mutation, an insertion mutation, a translocation, a missense mutation or a splice site mutation resulting in a change in the amino acid sequence (coding mutation).

The mutations may be identified by Exome sequencing, RNA-seq, whole genome sequencing and/or targeted gene panel sequencing and or routine Sanger sequencing of single genes. Suitable methods are known in the art.

Descriptions of Exome sequencing and RNA-seq are provided by Boa et al. (Cancer Informatics. 2014; 13(Suppl 2):67-82.) and Ares et al. (Cold Spring Harb Protoc. 2014 Nov. 3; 2014(11):1139-48); respectively. Descriptions of targeted gene panel sequencing can be found in, for example, Kammermeier et al. (J Med Genet. 2014 November; 51(11):748-55) and Yap KL et al. (Clin Cancer Res. 2014. 20:6605). See also Meyerson et al., Nat. Rev. Genetics, 2010 and Mardis, Annu Rev Anal Chem, 2013. Targeted gene sequencing panels are also commercially available (e.g. as summarised by Biocompare ((http://www.biocompare.com/Editorial-Articles/161194-Build-Your-Own-Gene-Panels-with-These-Custom-NGS-Targeting-Tools/)).

Sequence alignment to identify nucleotide differences (e.g. SNVs) in DNA and/or RNA from a tumour sample compared to DNA and/or RNA from a non-tumour sample may be performed using methods which are known in the art. For example, nucleotide differences compared to a reference sample may be performed using the method described by Koboldt et al. (Genome Res. 2012; 22: 568-576). The reference sample may be the germline DNA and/or RNA sequence.

CLONAL NEO-ANTIGENS

The present inventors have determined that intratumour heterogeneity (ITH) can cause variation between the neo-antigens expressed in different regions of a tumour and between different cells in a tumour. In particular, the inventors have determined that, within a tumour, certain neo-antigens are expressed in all regions and essentially all cells of the tumour whilst other neo-antigens are only expressed in a subset of tumour regions and cells.

As such, a "clonal" or "truncal" neo-antigen is a neo-antigen which is expressed effectively throughout a tumour and encoded within essentially every tumour cell. A "sub-clonal" or "branched" neo-antigen is a neo-antigen which is expressed in a subset or a proportion of cells or regions in a tumour.

References herein to "essentially all" are intended to encompass the majority of tumour cells in a subject. For example, this may comprise 60-100% of cells, e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of tumour cells in a subject.

"Present throughout a tumour", "expressed effectively throughout a tumour" and "encoded within essentially every tumour cell" may mean that the clonal neo-antigen is expressed in all regions of the tumour from which samples are analysed.

It will be appreciated that a determination that a mutation is "encoded within essentially every tumour cell" refers to a statistical calculation and is therefore subject to statistical analysis and thresholds.

Likewise, a determination that a clonal neo-antigen is "expressed effectively throughout a tumour" refers to a statistical calculation and is therefore subject to statistical analysis and thresholds.

"Expressed effectively in essentially every tumour cell or essentially all tumour cells" may mean that the mutation is present all tumour cells analysed in a sample, as determined using appropriate statistical methods.

By way of example, the cancer cell fraction (CCF), describing the proportion of cancer cells that harbour a mutation may be used to determine whether mutations are clonal or branched. For example, the cancer cell fraction may be determined by integrating variant allele frequencies with copy numbers and purity estimates as described by Landau et al. (Cell. 2013 Feb. 14; 152(4):714-26).

In brief, CCF values are calculated for all mutations identified within each and every tumour region analysed. If only one region is used (i.e. only a single sample), only one set of CCF values will be obtained. This will provide information as to which mutations are present in all tumour cells within that tumour region, and will thereby provide an indication if the mutation is clonal or branched. All sub clonal mutations (i.e. CCF<1) in a tumour region are determined as branched, whilst clonal mutations with a CCF=1 are determined to be clonal.

As stated, determining a clonal mutation is subject to statistical analysis and threshold. As such, a mutation may be identified as clonal if it is determined to have a CCF 95% confidence interval >=0.60, for example 0.65, 0.70, 0.75, 0.80, 0.85, 0.90, 0.95, 1.00 or >1.00. Conversely, a mutation may be identified as branched if it is determined to have a CCF 95% confidence interval <=0.60, for example 0.55, 0.50, 0.45, 0.40, 0.35, 0.30, 0.25, 0.20, 0.15, 0.10, 0.05 or 0.01, in any sample analysed.

It will be appreciated that the accuracy of a method for identifying clonal mutations is increased by identifying clonal mutations for more than one sample isolated from the tumour.

TUMOUR SAMPLES

Isolation of biopsies and samples from tumours is common practice in the art and may be performed according to any suitable method, and such methods will be known to one skilled in the art.

The method of this aspect may comprise, for example, determining the mutations present in cancer cells from one or more tumour regions isolated from a tumour. For example, the mutations present in a single biopsy, or alternatively, at least two, at least three, at least four, at least five, at least six, at least seven, at least eight, at least nine or at least ten or more biopsies isolated from a tumour may be determined.

The individual tumour samples may be isolated from different regions located throughout a tumour within a primary site or between primary and metastases or within a metastasis or between metastases. For example, determining the mutations present in tumours which are known to display morphological disparate histology in different regions may involve determining the mutations present in a number of individual samples isolated from morphologically disparate regions.

The sample may be a blood sample. For example, the blood sample may comprise circulating tumour DNA, circulating tumour cells or exosomes comprising tumour DNA.

SUBJECT SUITABLE FOR TREATMENT

The invention provides a method for identifying a subject with cancer who is suitable for treatment with an immune checkpoint intervention, said method comprising determining the number of clonal neo-antigens in one or more cancer cells from said subject, wherein a high number of clonal neo-antigens is indicative of response to an immune checkpoint intervention.

As used herein, the term "suitable for treatment" may refer to a subject who is more likely to respond to treatment with an immune checkpoint intervention, or who is a candidate for treatment with an immune checkpoint intervention. A subject suitable for treatment may be more likely to respond to said treatment than a subject who is determined not to be suitable using the present invention. A subject who is determined to be suitable for treatment according to the present invention may demonstrate a durable clinical benefit (DCB), which may be defined as a partial response or stable disease lasting for at least 6 months, in response to treatment with an immune checkpoint intervention.

The number of clonal neo-antigens identified or predicted in the cancer cells obtained from the subject may be compared to one or more pre-determined thresholds. Using such thresholds, subjects may be stratified into categories which are indicative of the degree of response to treatment.

A threshold may be determined in relation to a reference cohort of cancer patients. The cohort may comprise 10, 25, 50, 75, 100, 150, 200, 250, 500 or more cancer patients. The cohort may be any cancer cohort. Alternatively the patients may all have the relevant or specific cancer type of the subject in question.

In one embodiment, a "high" number of clonal neo-antigens means a number greater than the median number of clonal neo-antigens predicted in a reference cohort of cancer patients, such as the minimum number of clonal neo-antigens predicted to be in the upper quartile of the reference cohort.

In another embodiment, a "high" number of clonal neo-antigens may be defined as 10, 20, 30, 40, 50, 55, 60, 65, 70, 75, 80, 85, 90, 95, 100, 110, 120, 130, 140, 150, 160, 170, 180, 190 or 200 or more clonal neo-antigens.

A skilled person will appreciated that references to "high" or "higher" numbers of clonal neo-antigens may be context specific, and could carry out the appropriate analysis accordingly.

The invention further provides a method for identifying a subject with cancer who is suitable for treatment with an immune checkpoint intervention, said method comprising determining the ratio of clonal:sub-clonal neo-antigens and/or sub-clonal neo-antigen fraction in more than one cancer cell subject, wherein a high ratio of clonal:sub-clonal neo-antigens or lower/low sub-clonal neo-antigen fraction is indicative of to response to an immune checkpoint intervention.

As above, the clonal:sub-clonal ratio may be within the context of a cohort of subjects, either with any cancer or with the relevant/specific cancer. Accordingly, the clonal:sub-clonal neo-antigen ratio may be determined by applying methods discussed above to a reference cohort. A "high" or "higher" clonal:sub-clonal ratio may therefore correspond to a number greater than the median clonal:sub-clonal ratio predicted in a reference cohort of cancer patients, such as the minimum clonal:sub-clonal ratio predicted to be in the upper quartile of the reference cohort.

In another embodiment, a "high" or "higher" clonal:sub-clonal ratio means a ratio in the range of 3:1 to 100:1, such as a ratio of at least 3:1, 5:1, 10:1, 15:1, 20:1, 25:1, 50:1, 75:1 or 100:1. One skilled in the art will appreciate that the values may depend on the cohort in question.

The fraction of subclonal neo-antigens may also be defined in relation to a reference cohort, as discussed above. For example, a "lower" or "low" fraction of subclonal neo-antigens may correspond to a fraction smaller than the median fraction of subclonal neo-antigens predicted in a reference cohort of cancer patients, such as the maximum number predicted to be in the bottom quartile of the cohort.

Alternatively, one skilled in the art will appreciate that a sub-clonal neo-antigen fraction can be determined (for example for each patient) by dividing the number of sub-clonal neoantigens (for example that are predicted in the one or more cancer cells from said subject) by the number of total neoantigens (for example that are predicted in the one or more cancer cells from said subject).

In one embodiment, a "lower" or "low" fraction of subclonal neo-antigens may mean a fraction of 25% or less, such as a fraction of 20, 15, 10, 5, 3, 2 or 1% or less.

In a preferred embodiment, the method may comprise determining both the number of clonal neo-antigens and the ratio of clonal:sub-clonal neo-antigens or the fraction of of sub-clonal neo-antigens. As shown in the Example, combining measures of both neo-antigen burden and neo-antigen sub-clonal fraction was able to predict sensitivity to pembrolizumab better than either measure alone (see FIG. 4C), and outcome could be predicted in almost all cases (FIG. 4G-H).

According the invention provides a method method for identifying a subject with cancer who is suitable for treatment with an immune checkpoint intervention, said method comprising:
  (i) determining the number of clonal neo-antigens in one or more cancer cells from said subject; and
  (ii) determining the ratio of clonal:sub-clonal neo-antigens and/or sub-clonal neo-antigen fraction in more than one cancer cell from said subject;
wherein a higher number of clonal neo-antigens and a higher ratio of clonal:sub-clonal neo-antigens, or lower (or low) sub-clonal neo-antigen fraction, is indicative of response to an immune checkpoint intervention.

Furthermore, the present inventors have found that, surprisingly, tumour cells with high numbers of clonal neo-antigens exhibit similar expression profiles of immune checkpoint molecules, that is they exhibit a common expression profile of immune checkpoint molecules. As such, approaches to identify particular immune checkpoint molecules whose expression is increased or decreased relative to non-cancerous cells can also be used to identify patients likely to respond to checkpoint blockade therapies.

Therefore, in one aspect the invention provides a method for identifying subjects who have cancer who are more likely to respond to immune checkpoint interventions, comprising determining the expression profile of immune checkpoint molecules in cancer cells from said subject, or tumour type.

In one aspect the method comprises determining the expression profile of immune checkpoint molecules in the tumour, for example by identifying differentially expressed genes, e.g. relative to a suitable reference sample. The reference sample in respect of differential immune checkpoint molecule expression may be a non-cancerous cell or tumour, (e.g. with low clonal neoantigen burden) or peripheral blood lymphocytes.

For example, the expression profile of the immune checkpoint molecules may be determined by:
  (i) determining the RNA sequence of a sample isolated from the tumour; and/or
  (ii) performing a transcriptome-wide differential gene expression analysis to identify differential expression of immune checkpoint-related genes (e.g. adjusted to $p<0.05$).

Non-cancer cell data may be used as a comparison, for example from the same patient or from a standard reference.

The invention further provides a method for determining the expression profile of immune checkpoint molecules in a particular cancer type comprising the steps of:
  (i) obtaining RNA-sequencing data from the Cancer Genome Atlas (TCGA) data portal for a cohort of patients with the cancer of interest;
  (ii) obtaining Level_3 gene-level data from each patient;
  (iii) inputting the raw read counts into the package DESeq2 for analysis; and
  (iv) performing a transcriptome-wide differential gene expression analysis to identify significantly differentially expressed (adjusted $p<0.05$) immune checkpoint-related genes.

The invention thus provides a method for identifying subjects who have cancer who are more likely to respond to immune checkpoint interventions, comprising determining the expression profile of immune checkpoint molecules in cancer cells from said subject, or tumour type, using said method.

Figure 1B:
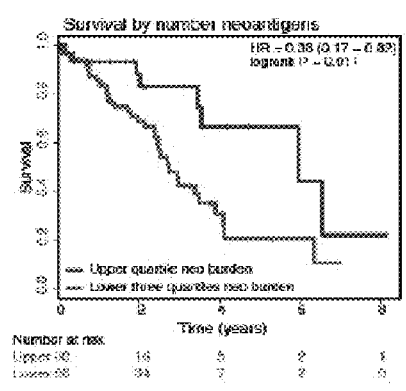
Figure 1C:
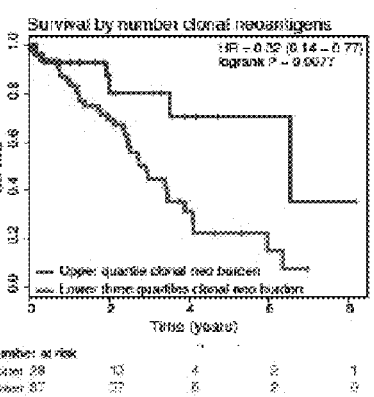
Figure 1D:
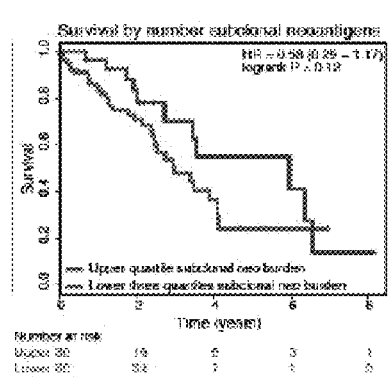
Figure 1E:
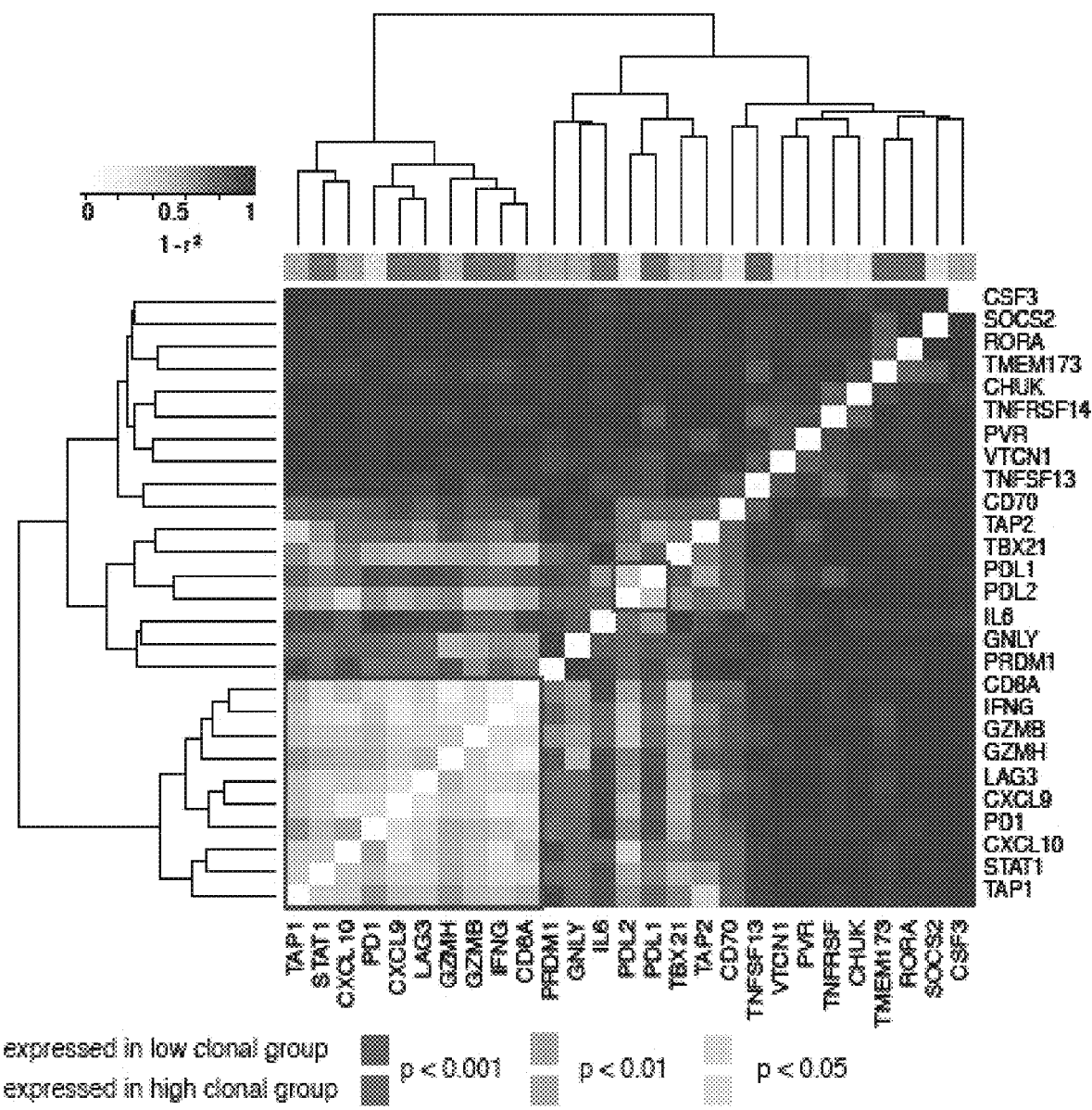

In a preferred aspect, differentially expressed genes between tumours with high clonal neo-antigen burden and low clonal neo-antigen burden are identified (see e.g. FIG. 1E). Thus, information regarding the number of clonal neo-antigens is informative and facilitates the combining of the two approaches, namely identifying and targeting subjects/tumours with a high number of clonal neo-antigens, and further investigating the gene expression of immune checkpoint molecules in those subjects/tumours with a high level of clonal neo-antigens. This facilitates a "double-pronged" therapeutic attack.

In one aspect, said differential immune expression is upregulation or high expression of an immune checkpoint molecule which is an inhibitory receptor or costimulatory receptor compared to a suitable reference sample, wherein such upregulation or high expression is indicative of a response to immune checkpoint interventions targeting the immune checkpoint molecule that has been upregulated or shown high expression.

Gene expression profiles may, for example, be determined by a method as described in present Example 1.

In a preferred embodiment the immune checkpoint molecule is PD-1 and/or LAG-3. In a particularly preferred embodiment the subject has lung cancer, preferably non small-cell lung cancer.

In an alternative embodiment, the immune checkpoint molecule is CTLA4.

In a preferred embodiment the cancer is lung cancer or melanoma, preferably non small-cell lung cancer or melanoma.

This method may also be used in combination with the previously described methods for identifying a subject with cancer who is likely to respond to treatment with an immune checkpoint intervention.

Accordingly the invention provides a method for identifying a subject with cancer who is suitable for treatment with an immune checkpoint intervention, said method comprising:
  (i) determining the number of clonal neo-antigens in one or more cancer cells from said subject; and
  (ii) determining the expression profile of immune checkpoint molecules in cancer cells and/or tumour infiltrating immune cells from said subject, or tumour type,
wherein a higher number of clonal neo-antigens and differential immune checkpoint molecule expression in comparison to a reference sample is indicative of response to an immune checkpoint intervention.

Method of Prognosis

The present inventors have made the important and surprising determination that cancer patients with higher numbers of clonal neo-antigens, and/or a higher ratio of clonal:sub-clonal neoantigens or a low sub-clonal neo-antigen fraction, have improved prognosis.

One skilled in the art would appreciate in the context of the present invention that subjects with high or higher numbers of clonal neo-antigens, for example within a cohort of subjects or within a range identified using a number of different subjects or cohorts, may have improved survival relative to subjects with lower numbers of clonal neo-antigens.

A reference value for the number of clonal neo-antigens could be determined using the following method, with a "high number" or "higher number" being anything above that.

Said method may involve determining the number of clonal neo-antigens predicted in a cohort of cancer subjects and either:
  (i) determining the median number of clonal neo-antigens predicted in that cohort; wherein that median number is the reference value; or
  (ii) determining the minimum number of clonal neo-antigens predicted to be in the upper quartile of that cohort, wherein that minimum number is the reference value. (See e.g. TCGA data analysis in the present Examples.)

Such a "median number" or "minimum number to be in the upper quartile" could be determined in any cancer cohort per se, or alternatively in the relevant/specific cancer types.

Alternatively, a "high" or "higher" number of clonal neo-antigens may be defined as 50, 55, 60, 65, 70, 75, 80, 85, 90, 95, 100, 110, 120, 130, 140, 150, 160, 170, 180, 190 or 200 or more clonal neo-antigens.

One skilled in the art would appreciate that references to "high" or "higher" numbers of clonal neo-antigens may be context specific, and could carry out the appropriate analysis accordingly.

As such, the present invention also provides a method for predicting or determining the prognosis of a subject with cancer, comprising determining the number of clonal neo-antigens in one or more cancer cells from the subject, wherein a higher number of clonal neo-antigens, for example relative to a cohort as discussed above, is indicative of improved prognosis. In a preferred embodiment the cancer is lung cancer or melanoma, preferably non small-cell lung cancer or melanoma.

In an alternative embodiment the invention comprises a method for predicting or determining the prognosis of a subject with cancer, the method comprising determining the clonal:sub-clonal ratio and/or sub-clonal neo-antigen fraction in more than one cancer cell from said subject, wherein a higher clonal:sub-clonal ratio and/or a lower/low sub-clonal neo-antigen fraction, for example relative to a cohort as discussed above, is indicative of improved prognosis. In a preferred embodiment the cancer is melanoma or lung cancer, preferably melanoma or non small-cell lung cancer.

TREATMENT OF CANCER

The present invention also provides a method of treating or preventing cancer in a subject, wherein said method comprises the following steps:
  i) identifying a subject with cancer who is suitable for treatment with an immune checkpoint intervention according to the method of the invention; and
  ii) treating said subject with an immune checkpoint intervention.

As defined herein "treatment" refers to reducing, alleviating or eliminating one or more symptoms of the disease, disorder or infection which is being treated, relative to the symptoms prior to treatment.

"Prevention" (or prophylaxis) refers to delaying or preventing the onset of the symptoms of the disease, disorder or infection. Prevention may be absolute (such that no disease occurs) or may be effective only in some individuals or for a limited amount of time.

The term "immune checkpoint intervention" is used herein to refer to any therapy which interacts with or modulates an immune checkpoint molecule. For example, an immune checkpoint intervention may also be referred to herein as a "checkpoint blockade therapy", "checkpoint modulator" or "checkpoint inhibitor".

By "inhibitor" is meant any means to prevent inhibition of T cell activity by these pathways. This can be achieved by antibodies or molecules that block receptor ligand interaction, inhibitors of intracellular signalling pathways, and compounds preventing the expression of immune checkpoint molecules on the T cell surface.

Checkpoint inhibitors include, but are not limited to, CTLA-4 inhibitors, PD-1 inhibitors, PD-L1 inhibitors, Lag-3 inhibitors, Tim-3 inhibitors, TIGIT inhibitors and BTLA inhibitors, for example. Co-stimulatory antibodies deliver positive signals through immune-regulatory receptors including but not limited to ICOS, CD137, CD27 OX-40 and GITR.

Examples of suitable immune checkpoint interventions include pembrolizumab, nivolumab, atezolizumab and ipilimumab.

As shown in Example 1 (see FIGS. 5A-C and 7A-G), lung tumours with a high number of clonal neoantigens express high levels of PD-1 and Lag-3, and in keeping, T cells reactive to clonal neoantigens in lung cancer subjects also express high levels of PD-1 and LAG-3. The co-expression of PD-1 and Lag-3 in tumours with high clonal neo-antigen burden versus low clonal burden suggests that simultaneous targeting of both pathways may generate maximal benefit.

Hence, in one aspect the invention relates to co-targeting PD-1 and Lag-3 pathways, for example in lung cancer, either by co-administration of inhibitors targeting each pathway or by administration of a single reagent targeting both pathways. As an example of the latter, bispecific antibodies are able to bind to PD-1 and Lag-3, or PD-L1 and Lag-3.

In a preferred embodiment of the present invention, the subject is a mammal, preferably a cat, dog, horse, donkey, sheep, pig, goat, cow, mouse, rat, rabbit or guinea pig, but most preferably the subject is a human.

In one aspect the method of treatment or prevention of cancer according to the invention comprises the step of identifying a patient in need of said treatment or therapy.

The cancer may be selected from, for example, bladder cancer, gastric cancer, oesophageal cancer, breast cancer, colorectal cancer, cervical cancer, ovarian cancer, endometrial cancer, kidney cancer (renal cell), lung cancer (small cell, non-small cell and mesothelioma), brain cancer (e.g. gliomas, astrocytomas, glioblastomas), melanoma, lymphoma, small bowel cancers (duodenal and jejunal), leukemia, pancreatic cancer, hepatobiliary tumours, germ cell cancers, prostate cancer, head and neck cancers, thyroid cancer and sarcomas.

In a preferred embodiment of the invention the cancer is lung cancer. In a particularly preferred embodiment the lung cancer is non-small cell lung cancer.

In one embodiment of the invention the cancer is melanoma.

In one aspect of the invention, the subject has pre-invasive disease, or is a subject who has had their primary disease resected who might require or benefit from adjuvant therapy, such as that provided by the present invention.

Treatment using the methods of the present invention may also encompass targeting circulating tumour cells and/or metastases derived from the tumour.

The methods and uses for treating cancer according to the present invention may be performed in combination with additional cancer therapies. In particular, the immune checkpoint interventions according to the present invention may be administered in combination with co-stimulatory antibodies, chemotherapy and/or radiotherapy, targeted therapy or monoclonal antibody therapy.

The invention will now be further described by way of Examples, which are meant to serve to assist one of ordinary skill in the art in carrying out the invention and are not intended in any way to limit the scope of the invention.

EXAMPLES

Example 1

The clinical relevance of neo-antigens and immune modulation within the context of NSCLC ITH, and the identity of neo-antigen-reactive tumour-infiltrating T cells was investigated.

Materials and Methods

Description of Patient Cohorts

Samples for sequencing (L011 and L012) were obtained from patients diagnosed with non-small cell lung cancer (NSCLC) who underwent definitive surgical resection prior to receiving any form of adjuvant therapy, such as chemotherapy or radiotherapy. Informed consent allowing for genome sequencing had been obtained. Both samples were collected from University College London Hospital, London (UCLHRTB 10/H1306/42) and were subjected to pathology review to establish the histological subtype: one tumour was classified with CK7+/TTF1+ adenocarcinoma (L011) and one tumour (L012) with squamous cell carcinoma histology. Detailed clinical characteristics are provided in table 51.

Samples obtained from (1) reflected a patient cohort of stage IV NSCLC, and a detailed description of this patient cohort, including tumour processing, can be found in supplementary material of (1). Detailed clinical characteristics of this cohort are provided in table S3.

Clinical Efficacy Analysis

Clinical efficacy analysis was performed as in (1). In brief, objective response to pembrolizumab was assessed by investigator-assessed immunerelated response criteria (irRC) by a study radiologist. As outlined in protocol, CT scans were performed every nine weeks. Partial and complete responses were confirmed by a repeat imaging occurring a minimum of 4 weeks after the initial identification of response; unconfirmed responses were considered stable or progressive disease dependent on results of the second CT scan. Durable clinical benefit (DCB) was defined as stable disease or partial response lasting longer than 6 months (week 27, the time of third protocol-scheduled response assessment). No durable benefit (NDB) was defined as progression of disease 6 months of beginning therapy. For patients with ongoing response to study therapy, progression-free survival was censored at the date of the most recent imaging evaluation. For alive patients, overall survival was censored at the date of last known contact. Details regarding response for each patient can be found in table S2.

TCGA Exome Data Sets

Tumour samples, with mutation calls and HLA typing described below, were obtained from the Cancer Genome Atlas (TCGA) for a cohort of lung adenocarcinoma (LUAD, n=124) and lung squamous cell carcinoma (LUSC, n=124). SNV data was obtained from TumourPortal (2) for the LUAD and LUSC TCGA cohorts (http://www.tumourportal.org/tumour_types? ttype=LUAD|LUSC). One LUAD patient, TCGA-05-4396, was excluded for having over 7000 low quality mutations called, mostly in a C[C>G]G context. A LUSC patient, TCGA-18-3409, was excluded for bearing a strong UV signature, uncharacteristic of a LUSC tumour.

Tumour Processing

For both L011 and L012 four primary tumour regions from a single tumour mass, separated by 1 cm intervals, and adjacent normal tissue were selected by a pathologist, documented by photography, and snap-frozen. For the brain metastasis in L011, four tumour regions as determined by hematoxylin and eosin (H&E) staining, were selected by a pathologist in the form of formalin-fixed, paraffin-embedded (FFPE) tissue blocks. Peripheral blood was collected at the time of surgery from all patients and snap-frozen. Approximately 5×5×5 mm snap-frozen tumour tissue and 500 μl of blood was used for genomic DNA extraction, using the DNeasy kit (Qiagen) according to manufacturer's protocol. For the FFPE tissue, manual blade macrodissection was used to remove tumour-rich areas of tissue from 10-40 μm unstained slides, aand DNA was extracted from this using the DNeasy Blood and Tissue kit (Qiagen) DNA was quantified by Qubit (Invitrogen) and DNA integrity was examined by agarose gel eletrophoresis. Details regarding processing of validation and discovery cohort can be found in supplementary material of (1).

Multi-Region Whole-Exome Sequencing and Variant Calling L012

For each tumour region and matched germ-line from patient L012, exome capture was performed on 1-2 μg DNA using the Illumina Nextera kit according to the manufacturer's protocol (Illumina). Samples were paired-end multiplex sequenced on the Illumina HiSeq 2500 at the Advanced Sequencing Facility at the LRI, as described previously (3, 4). Each captured library was loaded on the Illumina platform and paired-end sequenced to the desired average sequencing depth (mean across exomes=392.75). Raw paired end reads (100 bp) in FastQ format generated by the Illumina pipeline were aligned to the full hg19 genomic assembly (including unknown contigs) obtained from GATK bundle 2.8 (5), using bwa mem (bwa-0.7.7) (6). Picard tools v1.107 was used to clean, sort and merge files from the same patient region and to remove duplicate reads (http://broadinstitute.github.io/picard). Quality control metrics were obtained using a combination of picard tools (1.107), GATK (2.8.1) and FastQC (0.10.1) (http://www.bioinformatics.babraham.ac.uk/projects/fastqc/).

SAMtools mpileup (0.1.16) (7) was used to locate non-reference positions in tumour and germ-line samples. Bases with a phred score of <20 or reads with a mapping-quality <20 were skipped. BAQ computation was disabled and the coefficient for downgrading mapping quality was set to 50. Somatic variants between tumour and matched germ-line were determined using VarScan2 somatic (v2.3.6) (8) utilizing the output from SAMtools mpileup. Default parameters were used with the exception of minimum coverage for the germ-line sample that was set to 10, minimum variant frequency was changed to 0.01 and tumour purity was set to 0.5. VarScan2 processSomatic was used to extract the somatic variants. The resulting SNV calls were filtered for false positives using Varscan2's associated fpfilter.pl script, having first run the data through bam-readcount (0.5.1). Only INDEL calls classed as 'high confidence' by VarScan2 processSomatic were kept for further analysis.

All variants were manually reviewed using Integrated Genomics Viewers (IGV) (9), and those showing an Illumina specific error profile (10) were removed. Remaining variants were sequenced on Ion Torrent PGM sequencer (Life Technologies) to a median depth of 1513. For this an Ion AmpliSeq™ custom panel (Life Technologies) was designed using the online designer (www.ampliseq.com). Multiplex PCRs were performed on DNA from each region according to the manufacturer's protocol. Barcoded sequencing libraries were TM constructed, which were sequenced with 200 bp read length on the Ion Torrent PGM sequencer (Life Technologies). Sequence alignment to target regions from the hg19 genome was performed using the IonTorrent TorrentSuite™ software. Variants for which the coverage was 50 in at least one region were selected. A variant was considered to be present in a region if the variant frequency was ≥0.01 for SNVs and ≥0.02 for INDELS. Again manual review in IGV was performed and variants that passed this stage were used for subsequent analyses. All variants were annotated using ANNOVAR (11) and potential driver mutations were defined as described in (12).

L011

The sequencing and analysis of the germline, and primary tumour regions have previously been described in (13). Sequencing of the metastatic regions was performed by BGI Tech following the protocols described in (13). Computational processing of the metastatic regions was performed using the methods described for L012 above, with an average median depth across the samples of 93.7. The non-silent variants were manually reviewed using IGV as for L012.

Variant Calling from Rizvi Data

BAM files representing both the germline and tumour regions from (i) 16 samples representing the discovery cohort and 18 samples representing a validation cohort (Rizvi data), were obtained and converted to FASTQ format using picard tools (1.107) SamToFastq Alignment and variant calling was performed as described for L012 above.

Clonal Analysis

For TCGA samples, the clonal status of each mutation was estimated by integrating the wild-type and mutant allele counts, absolute major and minor copy numbers, and tumour purity estimates as previously described (14). For L011 and L012 clonal status of each mutation was estimated based on multiregion sequencing analysis. In brief, each mutation was classified as clonal if identified and present in each and every tumour region sequenced within the tumour. Conversely, any mutations not ubiquitously present in every tumour region was classified as subclonal.

For discovery and validation cohort tumour, encompassing data obtained from (1), the cancer cell fraction of each mutation was estimated by integrating the local copy number (obtained from ASCAT, see below), tumour purity (also obtained from ASCAT), and variant allele frequency. In brief, for a given mutation we first calculated the observed mutation copy number, nmut, describing the fraction of tumour cells carrying a given mutation multiplied by the number of chromosomal copies at that locus using the following formula:

$$n_{mut} = VAF \frac{1}{p}[pCN_t + CN_n(1-p)]$$

where VAF corresponds to the variant allele frequency at the mutated base, and p, $CN_t$, $CN_n$ are respectively the tumour purity, the tumour locus specific copy number, and the normal locus specific copy number. We then calculated the expected mutation copy number, $n_{chr}$, using the VAF and assigning a mutation to one of the possible copy numbers using maximum likelihood. We also assessed whether mutation copy number could be better explained by subclonal copy numbers when applicable. Ultimately, this allowed us to obtain modified variant and reference counts for every mutation, corrected for both copy number and tumour purity. All mutations were then clustered using the PyClone Dirichlet process clustering (15). Given that copy number and purity had already been corrected, we set integer copy numbers to 1 and purity to 1; allowing clustering to simply group clonal and subclonal mutations. We ran PyClone with 10,000 iterations and a burn-in of 1000, and default parameters. Notably, for assessing mutation clonal status, mutations were first further filtered to ensure reliable clustering. In brief, only mutations with a read depth of at least 10 in both germline and tumour were used, a Varscan2 somatic p-value threshold of 0.01. A minimum of 5 alternate reads was required for each variant, as well as a minimum tumour variant allele frequency of 1%. Mutations were also filtered such that a maximum of 2 germline reads, and 2% germline variant allele frequency was permitted.

For two tumours, ZA6965 and GR0134, reliable copy number, mutation and purity estimations could not be extracted, rendering clonal architecture analysis intractable and these tumours were omitted from the analysis Copy Number Analysis For data obtained from (1) processed sample exome SNP and copy number data from paired tumour-normal was generated using VarScan2 (v2.3.6). Varscan2 copy number was run using default parameters with the exception of min-coverage (21221095) and data-ratio. The data-ratio was calculated on a per-sample basis as described in (22300766). The output from Varscan was processed using the ASCAT v2.3 (20837533) to provide segmented copy number data and cellularity and ploidy estimates for all samples based on the exome sequence data. The following setting was altered from its default value: Threshold for setting ACF to 1 was adjusted from 0.2 to 0.15 and the package was run with gamma setting of 1. For TCGA samples, SNP6.0 data was processed to yield copy number information, as described in McGranahan, 2015.

Phylogenetic Tree Construction

The phylogenetic trees were built using binary presence/absence matrices built from the regional distribution of variants within the tumour, as described in (12). For tumour L011, the primary tumour data was reanalyzed using the method described for L012 and the L011 metastatic regions, allowing for a combined tree featuring both primary and metastatic regions.

HLA Typing of Patient Samples

For all TCGA patients, the 4-digit HLA type was determined using POLYSOLVER (POLYmorphic loci reSOLVER)(16). Patients L011 and L012 were serotyped and simultaneously genotyped using Optitype (17), which produced concordant results.

Identification of Putative Neo-Antigens

Identified non-silent mutations were used to generate a comprehensive list of peptides 9-11 amino acids in length with the mutated amino acid represented in each possible position.

The binding affinity of every mutant peptide and its corresponding wild-type peptide to the patient's germline HLA alleles was predicted using netMHCpan-2.8 (18, 19). Candidate neo-antigens were identified as those with a predicted binding strength of <500 nM.

TCGA Survival Analysis

Clinical data for the TCGA patients was accessed through the TCGA data portal and downloaded from https://tcgada-ta.nci.nih.gov/tcgafiles/ftp auth/distro ftpusers/anonymous/tumour/CANCER.T YPE /bcr/biotab/clin/. Survival analyses were performed in R using the survival package.

Differential Gene Expression Analysis

RNA-sequencing data was downloaded from the TCGA data portal. For each LUAD patient, all available level_3' gene-level data was obtained. The raw read counts were used as input into the R package DESeq2 for analysis. A transcriptomewide differential gene expression analysis was performed and significantly differentially expressed (adjusted p<0.05) immune related genes (listed in Table S1) were identified. These genes were clustered on their co-expression using the metric $1-r^2$.

Isolation of Tumour-Infiltrating Lymphocytes (TILs) for L011 and L012

Tumours were taken directly from the operating theatre to the department of pathology where the sample was divided into regions. Samples were subsequently minced under sterile conditions followed by enzymatic digestion (RPMI-1640 (Sigma) with Liberase TL research grade (Roche) and DNAse I (Roche)) at 37° C. for 30 minutes before mechanical dissociation using gentleMACS (Miltenyi Biotech). Resulting single cell suspensions were enriched for leukocytes by passage through a Ficoll-paque (GE Healthcare) gradient. Live cells were counted and frozen in human AB serum (Sigma) with 10% dimethyl sulfoxide at −80° C. before transfer to liquid nitrogen.

In-Vitro Expansion of Tumour-Infiltrating Lymphocytes for L011 and L012

TILs were expanded using a rapid expansion protocol (REP) in T25 flasks containing EX-VIVO media (Lonza) supplemented with 10% human AB serum (Sigma), soluble anti-CD3 (OKT3, BioXCell), 6000IU/mL recombinant human (rhIL-2, PeproTech) and $2 \times 10^7$ irradiated PBMCs (30 Gy) pooled from 3 allogeneic healthy donors. Fresh media containing rhIL-2 at 3000IU/mL was added every three days as required. Following 2 weeks of expansion, TILs were counted, phenotyped by flow cytometry and frozen in human AB serum (Sigma) at −80° C. before use in relevant assays or long-term storage in liquid nitrogen.

MHC Multimer Generation and Combinatorial Encoding-Flow Cytometry Analysis

MHC-multimers holding the predicted neoepitopes were produced in-house (Technical University of Denmark, laboratory of SRH). Synthetic peptides were purchased at Pepscan Presto, NL. HLA molecules matching the HLA-expression of L011 (HLA-A1101, A2402, and B3501) and L012 (HLA-A1101, A2402, and B0702) were refolded with a UV-sensitive peptide, and exchanged to peptides of interest following UV exposure (20-23). Briefly, HLA complexes loaded with UV-sensitive peptide were subjected to 366-nm UV light (CAMAG) for one hour at 4° C. in the presence of candidate neo-antigen peptide in a 384-well plate. Peptide-MHC multimers were generated using a total of 9 different fluorescent streptavidin (SA) conjugates: PE, APC, PE-Cy7, PE-CF594, Brilliant Violet (BV)421, BV510, BV605, BV650, Brilliant Ultraviolet (BUV)395 (BioLegend). MHC-multimers were generated with two different streptavidin-conjugates for each peptide-specificity to allow a combinatorial encoding of each antigen responsive T cells, enabling analyses for reactivity against up to 36 different peptides in parallel (24, 25).

Identification of Neo-Antigen-Reactive CD8+ T Cells

Figure 9A:
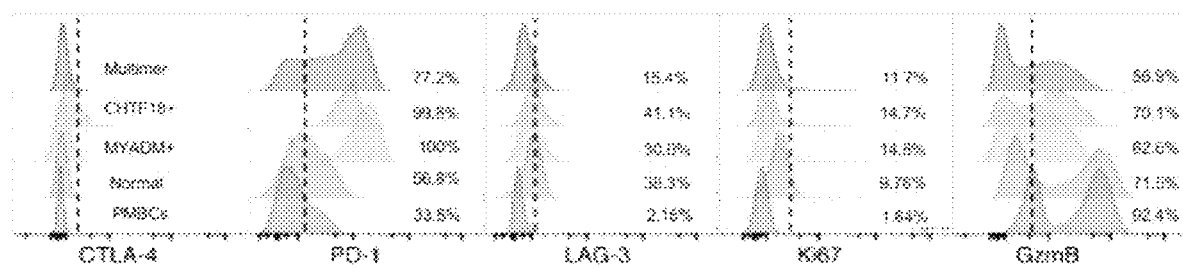
FIGS. 9A-FIG. 9D: Immunophenotype of tumour-infiltrating CD8+ T cells from patient L012 FIG. 9A) Activation and functional phenotype of tumour-infiltrating CD8+ CHTF18-reactive (CHTF18+) and MYADM-reactive (MYADM+) T cells versus MHC-multimer negative CD8+ T cells in tumour (Multimer-), normal tissue and PBMCs. Percentage of cells expressing CTLA-4, PD-1, LAG-3, Ki-67 and GzmB is shown. Histograms are generated from L012, region 2 and findings representative of all tumour regions.
Figure 9B:
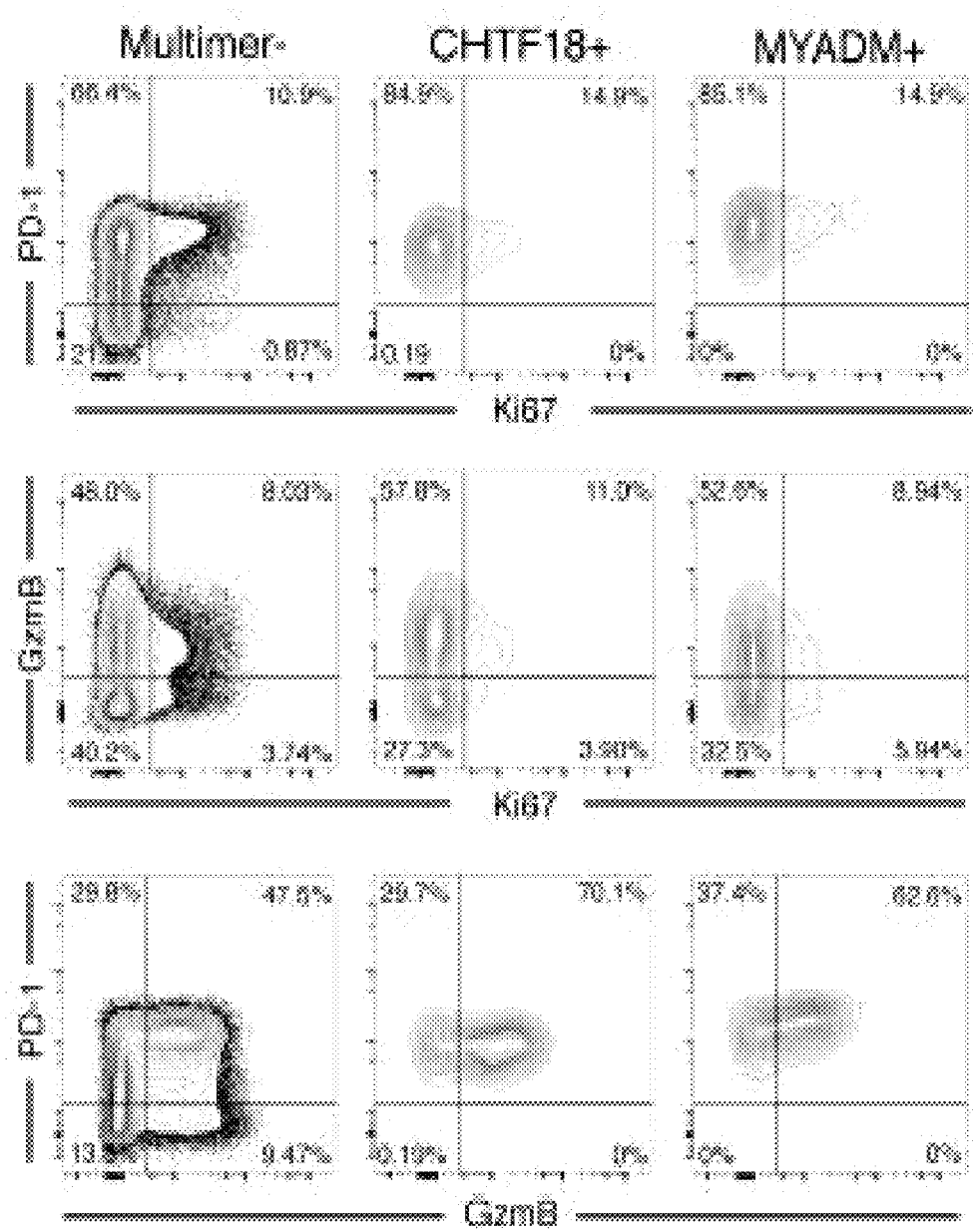
Figure 9C:
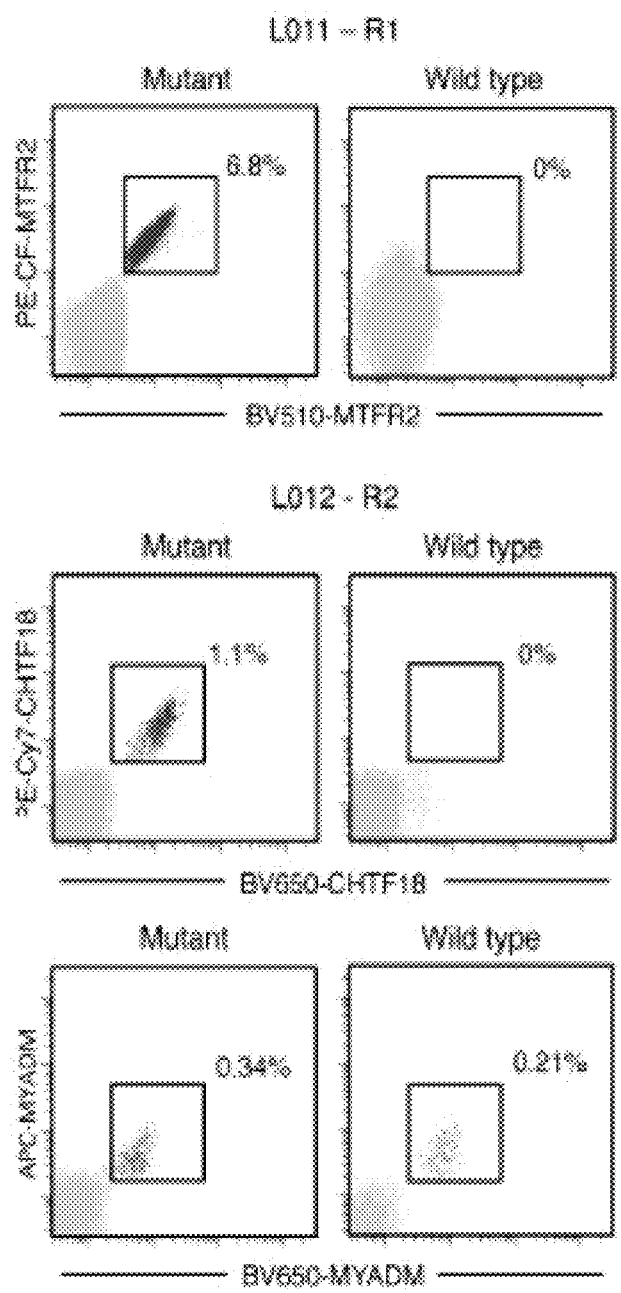
Figure 9D:
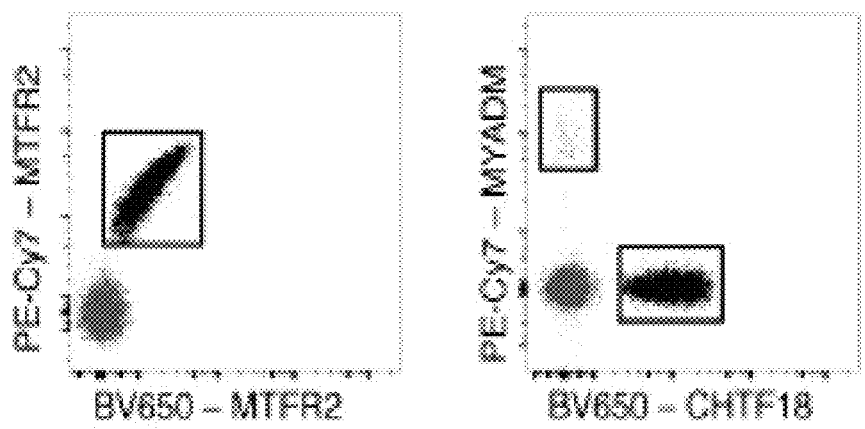

MHC-multimer analysis was performed on in-vitro expanded CD8+ T lymphocytes isolated from region-specific lung cancer samples and adjacent normal lung tissue. 290 and 355 candidate mutant peptides (with predicted HLA binding affinity <500 nM, including multiple potential peptide variations from the same missense mutation) were synthesized and used to screen expanded L011 and L012 TILs respectively. For staining of expanded CD8+ T lymphocytes, samples were thawed, treated with DNAse for 10 min, washed and stained with MHC multimer panels for 15 min at 37° C. Subsequently, cells were stained with LIVE/DEAD® Fixable Near-IR Dead Cell Stain Kit for 633 or 635 nm excitation (Invitrogen, Life Technologies), CD8-PerCP (Invitrogen, Life Technologies) and FITC coupled antibodies to a panel of CD4, CD14, CD16, CD19 (all from BD Pharmingen) and CD40 (AbD Serotec) for an additional 20 min at 4° C. Data acquisition was performed on an LSR II flow cytometer (Becton Dickinson) with FACSDiva 6 software. Cutoff values for the definition of positive responses were ≥0.005% of total CD8+ cells and ≥10 events. For patient L011, HLA-B3501 MTFR2-derived multimers were found to bind the mutated sequence FAFQEYDSF (netMHC binding score: 22) but not the wild type sequence FAFQEDDSF (netMHC binding score: 10) (FIGS. 11B and D, FIG. 9C). No responses were found against overlapping peptides AFQEYDSFEK and KFAFQEYDSF. For patient L012 HLA-A1101 CHTF18-derived multimers bound the mutated sequence LLLDIVAPK (netMHC binding score: 37) but not the wild type sequence: LLLDILAPK (netMHC binding score: 41) (FIGS. 11C and E, FIG. 9C). No responses were found against overlapping peptides CLLLDIVAPK and IVAPKLRPV. Finally, HLA-B0702 MYADM-derived multimers bound the mutated sequence SPMIVGSPW (netMHC binding score: 15) as well as the wild type sequence SPMIVGSPR (netMHC binding score: 1329). No responses were found against overlapping peptides SPMIVGSPWA, SPMIVGSPWAL, SPWALTQPLGL and SPWALTQPL.

MHC-Multimer Analysis and Multi-Parametric Flow Cytometric Phenotyping of Baseline, Non-Expanded Tumour Samples for L011 and L012

Tumour samples were thawed, washed and first stained with custom-made MHCmultimers for 10-15 minutes at 37° C. in the dark. Cells were thereafter transferred onto wet ice and stained for 30 minutes, in the dark, with a panel of surface antibodies used at the manufacturer's recommended dilution: CD8-V500, SK1 clone (BD Biosciences), PD-1-BV605, EH12.2H7 clone (Biolegend), CD3-BV785, OKT3 clone (Biolegend), LAG-3-PE, 3DS223H clone (eBioscience). Cells were permeablized for 20 minutes with use of the intracellular fixation and permeabilization buffer set from eBioscience. An intracellular staining panel was applied for 30 minutes, on ice, in the dark, and consisted of the following antibodies used at the manufacturers recommended dilution: granzyme B-V450, GB11 clone (BD Biosciences), FoxP3-PerCP-Cy5.5, PCH101 clone (eBioscience), Ki67-FITC, clone B56 (BD Biosciences) and CTLA-4-APC, L3D10 clone (Biolegend). Data acquisition was performed on a BD FACSAria III flow cytometer (BD Biosciences) and analysed in Flowjo version 10.0.8 (Tree Star Inc.).

Immunohistochemistry for L011 and L012

Samples from patients L011 and L012 and reactive human tonsils were fixed in buffered formalin and embedded in paraffin according to conventional histological protocols. 2-5 micrometer tissue sections from paraffin blocks were cut and transferred on electrically charged slides to subject to immunohistochemistry. Details of the primary used antibodies are listed in the below table. To establish optimal staining conditions (i.e. antibody dilution and incubation time, antigen retrieval protocols, suitable chromogen) each antibody was tested and optimized on sections of human reactive tonsil by conventional single immunohistochemistry using the automated platforms BenchMark Ultra (Ventana/Roche) and the Bond-III Autostainer (Leica Microsystems) according to a protocol described elsewhere (26, 27).

Where available, at least two distinct antibodies raised against the same protein were analyzed in tonsil to confirm the specificity of its staining pattern. For multiple staining a protocol previously described was carried out (28). For evaluation of protein co-expression in the cytoplasm or cell membrane, change of the single colour of the chromogen is noted i.e. blue and red gave rise to a purple and brown and blue to an almost black labelling. Immunohistochemistry and protein reactivity patterns were assessed by TM. Scoring of multiple immuno-staining was performed together with AF. Approval for this study was obtained from the National Research Ethics Service, Research Ethics Committee 4 (REC Reference number 09/H0715/64).

| Molecule | Antibody type | Clone name | Dilution | Source |
|---|---|---|---|---|
| Anti-human CD8 | Rabbit Monoclonal | SP239 | 1:100 | Spring Biosciences Inc., Pleasanton, CA, US |
| Anti-human FoxP3 | Mouse Monoclonal | 236A/E7 | 1:100 | Kind gift from Dr G Roncador, CNIO, Madrid (Spain) |
| Anti-human PD-L1 | Rabbit Monoclonal | SP142 | 1:50 | Spring Biosciences Inc., Pleasanton, CA, US |
| Anti-human LAG-3 | Mouse Monoclonal | 17B4 | 1:750 | LifeSpan Biosciences Inc., Nottingham, UK |
| Anti-human Granzyme B | Mouse Monoclonal | 11F1 | RTU | Leica Microsystems Ltd., Newcastle-upon-Tyne, UK |

Results

Figure 5A:
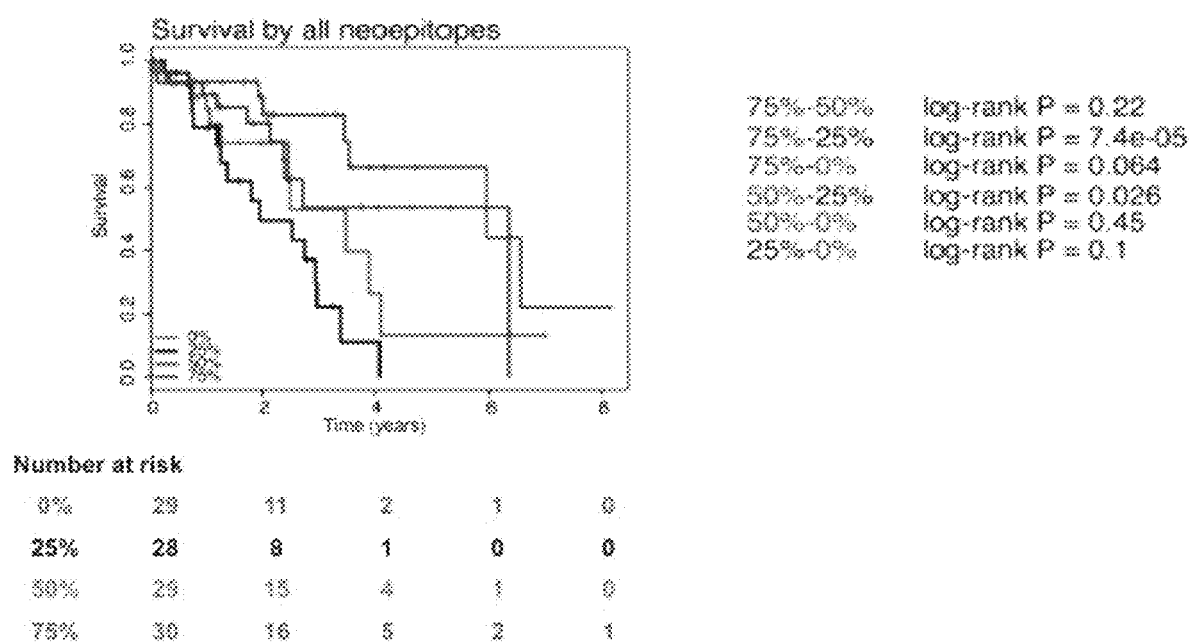
FIGS. 5A-FIG. 5C: Quartile Breakdown of LUAD Survival. Overall survival curves showing all four quartiles comparing patients on total neo-antigen load (FIG. 5A), clonal neo-antigen load (FIG. 5B), and subclonal neo-antigen load (FIG. 5C). Associated log-rank p-values between each quartile is given to the right of the plots.

A large tumour neo-antigen burden may increase tumour recognition by T cells, reducing the potential for immune-evasion (12). In support of the clinical relevance of tumour neo-antigens (7), it was found that high neo-antigen load (defined as the upper quartile of the number of neo-antigens predicted in the cohort) was associated with longer overall survival times in LUAD samples with matched clinical data (n=117) when compared to tumours in the remaining quartiles (FIG. 1B, logrank p=0.011; FIG. 5A).

Figure 5B:
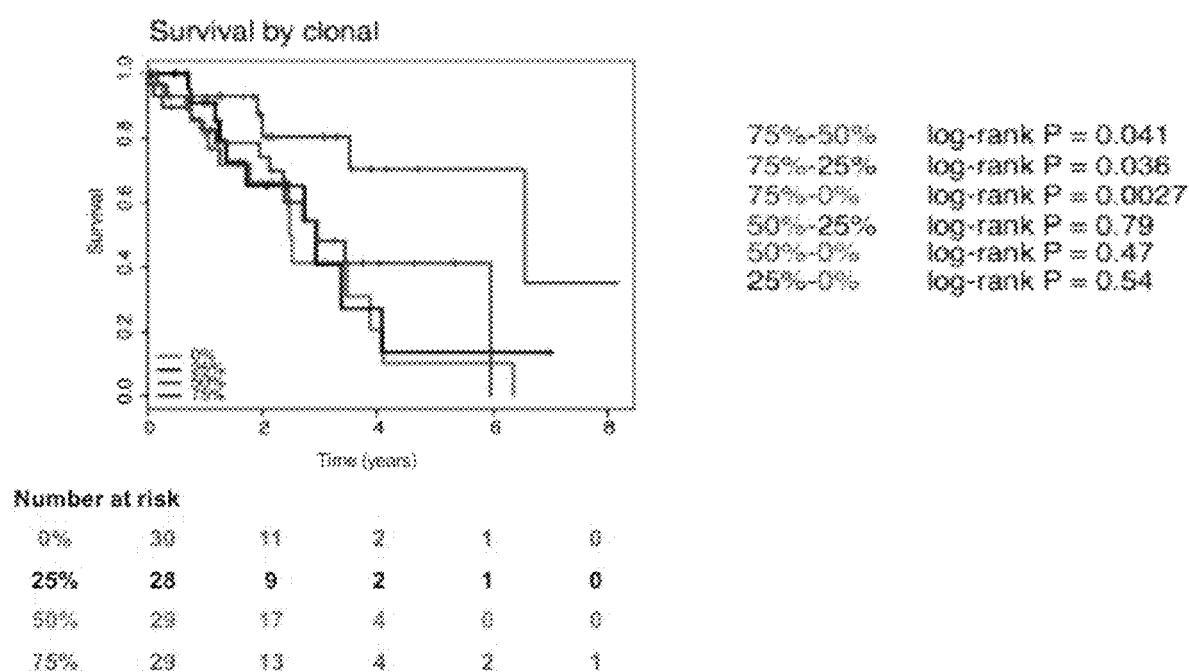
Figure 5C:
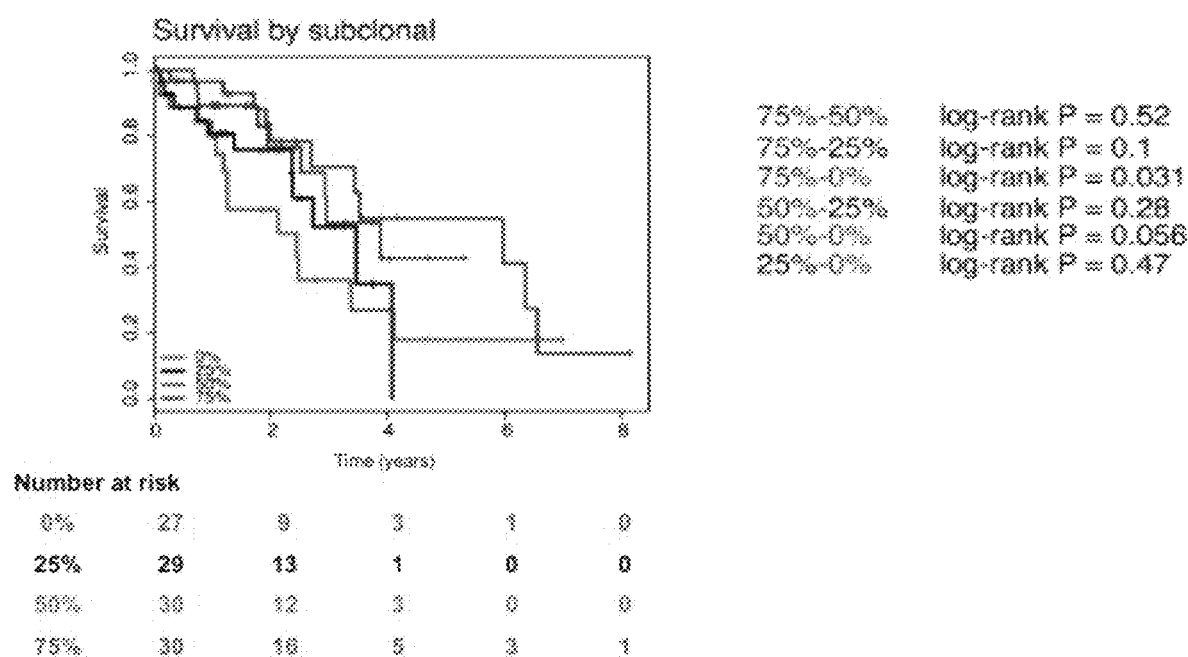
Figure 6A:
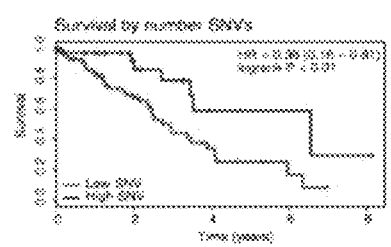
FIGS. 6A-FIG. 6C: Survival by number of SNVs in LUAD.
Figure 6B:
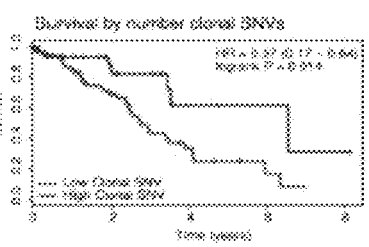
Figure 6C:
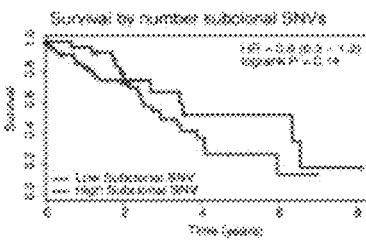
Figure 7A:
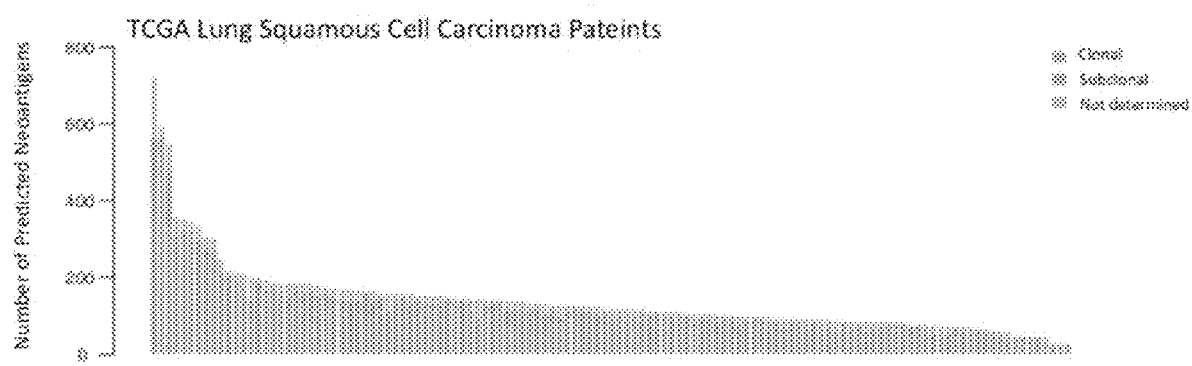
Figure 7D:
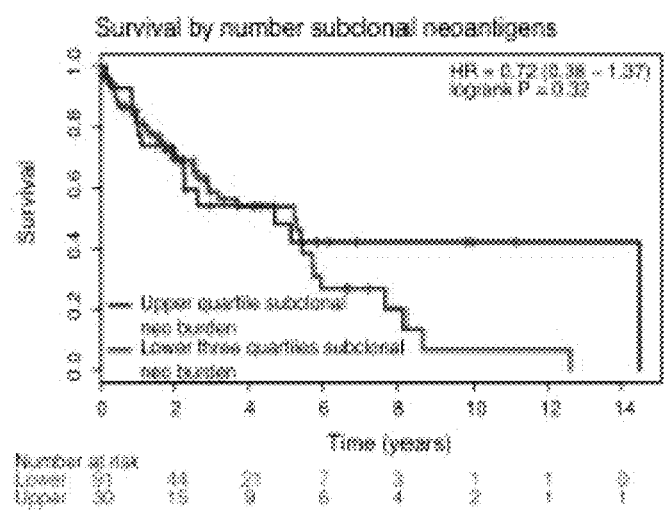
Figure 7E:
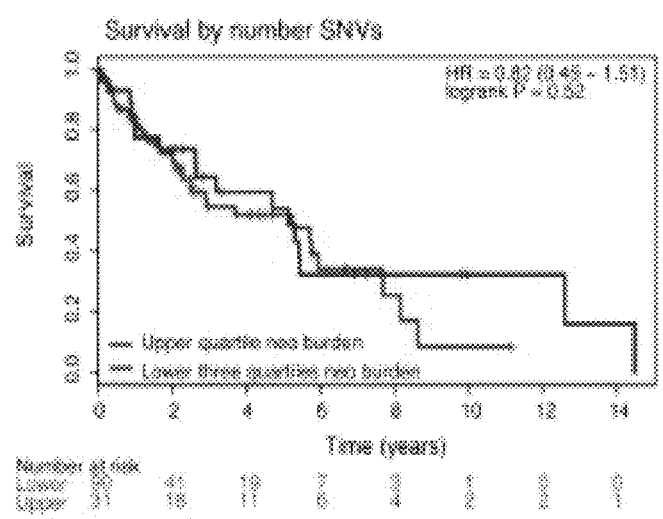
Figure 7F:
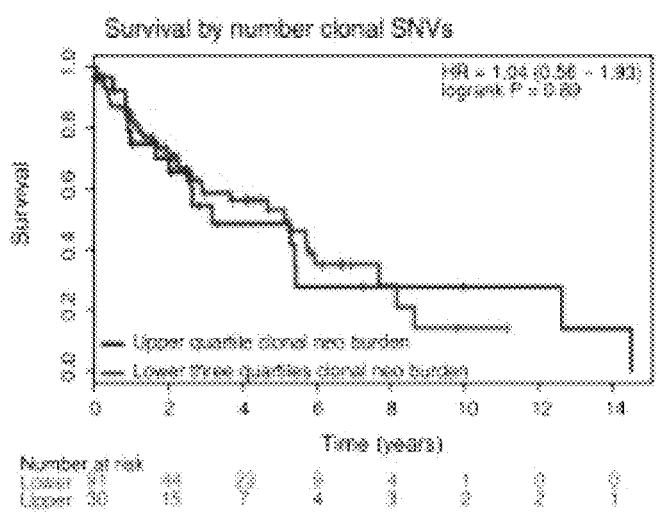
Figure 7G:
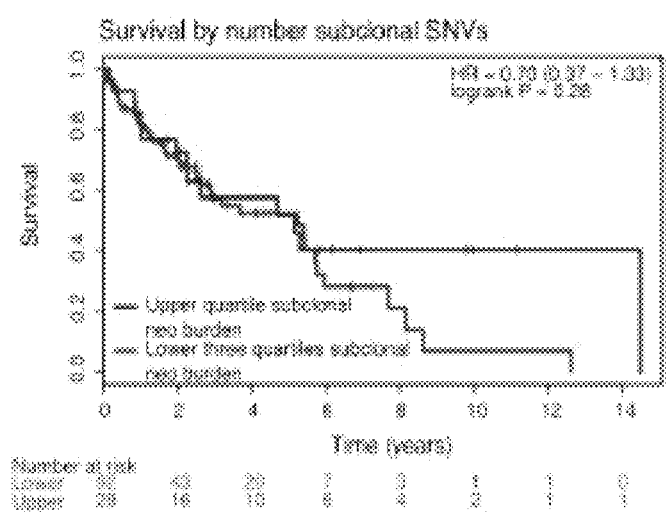

To determine whether neo-antigen clonal status (the presence of a neo-antigen in all tumour (clonal) compared to a subset of tumour cells (subclonal)) might influence the relationship with survival outcome, the cancer cell fraction (proportion of cancer cells harboring each mutation) was calculated and each putative neo-antigen was classified as either clonal or subclonal (13). Tumours harboring a high number of predicted clonal neo-antigens (defined as the upper quartile of the cohort) were associated with longer overall survival compared to all other tumours in the cohort (FIG. 1C, log-rank p=0.0077; FIG. 5B). Conversely, the number of predicted subclonal neo-antigens was not significantly associated with overall survival (FIG. 1D, log-rank p=0.12; FIG. 5C). Although neo-antigen burden was related to mutation burden, we observed a stronger relationship between overall survival and number of neo-antigens compared to number of mutations (FIGS. 6A-C). These data suggest the presence of a high number of clonal neo-antigens in LUAD may favor effective immunosurveillance. The LUSC cohort had a narrower range of putative neo-antigens (FIG. 7A), with a median absolute deviation of 50 and interquartile range of 71 and a statistically significant association between overall survival and neo-antigen load was not observed in this cohort (FIGS. 7B-G). This might reflect difficulties in dissecting the clonal architecture of tumours from single samples (14).

Figure 8:
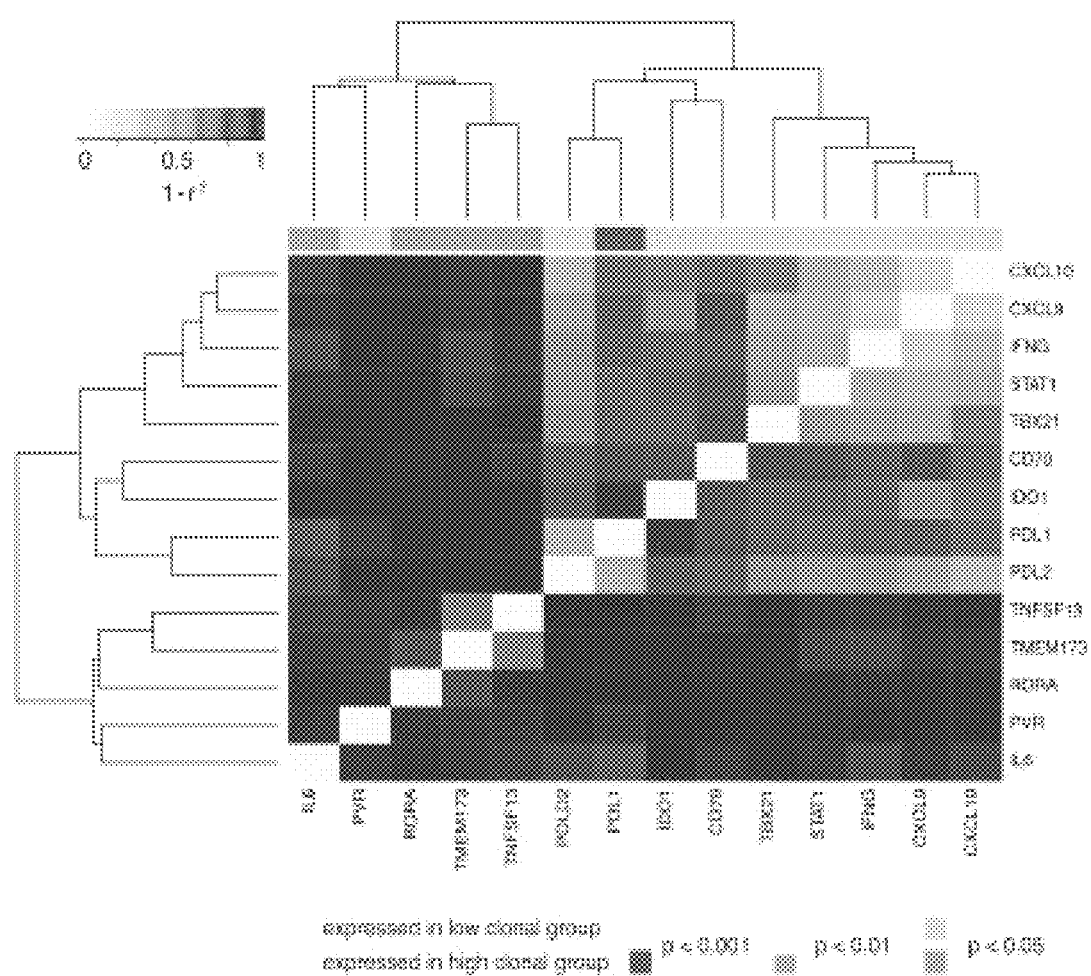
FIG. 8: Differential Gene Expression Analysis. Differentially expressed genes between the high clonal neo-antigen burden patients and remainder of cohort, clustered on coexpression.

Gene expression analysis revealed 27 immune-related genes differentially expressed between low (defined as the lower quartile of the number of clonal neo-antigens predicted in the cohort) and high clonal neo-antigen cohorts (Table S1). CD8A (p=0.005) and genes associated with antigen presentation (TAP-1p=0.003, STAT-1p<0.001), T cell infiltration (CXCL-10p=0.005, CXCL-9p=p<0.001) and effector T cell function (IFN-γ p<0.001, Granzymes B p<0.001 and H p=0.008) were up-regulated in the high clonal neo-antigen cohort and clustered together (FIG. 1E). PD-1 (p=0.02) and lymphocyte activation gene 3 (LAG-3, p<0.001), negative regulators of T cell function (15), were also identified in this cluster. PD-L1 was also significantly up-regulated (p<0.001) in the high clonal cohort, clustering with PD-L2. When we compared the high clonal neo-antigen tumours to all other tumours in the cohort, PD-L1 was identified as the most significantly differentially expressed immune gene (FIG. 8, p<0.001).

These data suggest that a high clonal neo-antigen burden is associated with the presence ofactivated effector T cells potentially regulated by the expression of specific immune checkpoint proteins (PD-1, LAG-3, PD-L1/2).

Figure 2A:
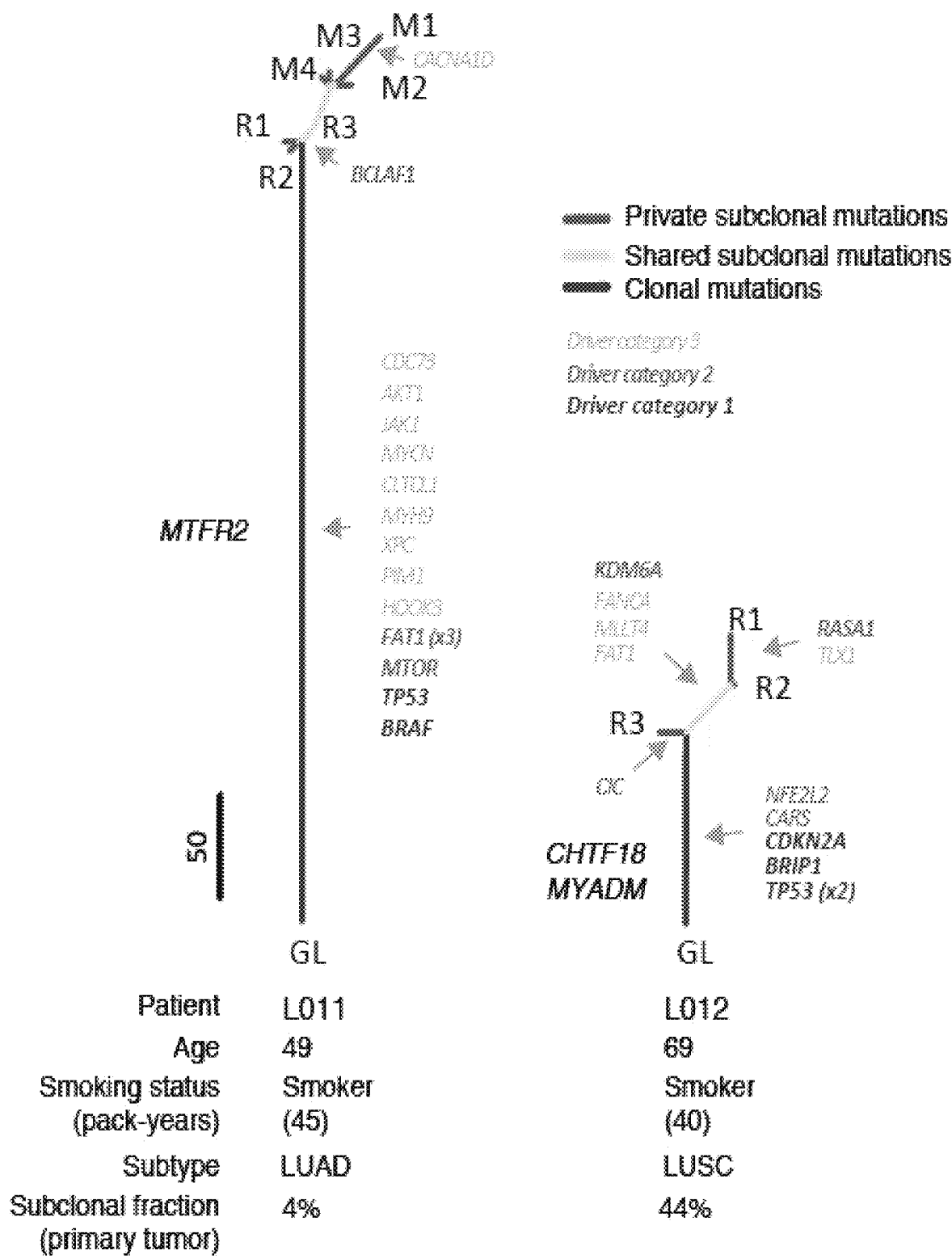
FIGS. 2A-FIG. 2E.
Figure 2B:
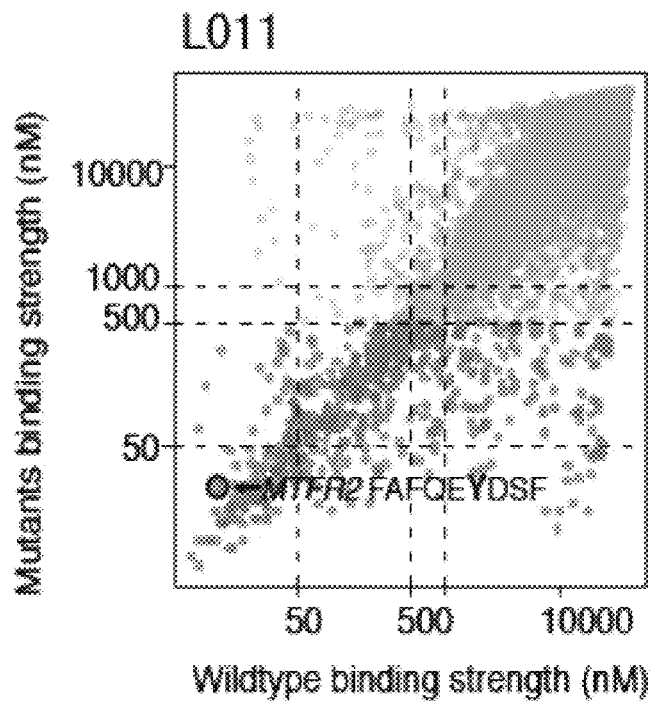

It was next addressed whether CD8+ T cells reactive to clonal neo-antigens could be identified in primary NSCLC tumours. Two early stage tumours, L011 and L012, subjected to multi-region exome sequencing (13), permitted phylogenetic analysis and prediction of neo-antigens within each primary tumour region (FIG. 2A). L011 included a brain metastasis, resected 14 months following primary surgery, subjected to multi-region sequencing. While both tumours were derived from female smokers (>40 pack-years), their mutation burden and extent of heterogeneity was distinct (FIG. 2A). L011, an adenocarcinoma, exhibited a homogenous primary tumour and metastatic dissemination to the brain (M1-M4), likely originating from tumour region R3 (FIG. 2A). A total of 313 neo-antigens were predicted within the primary tumour, 88% of which were clonal, identified in every region of the primary tumour (FIG. 2B). Conversely, L012, a squamous cell carcinoma, exhibited a low mutation burden and extensive heterogeneity, with 75% of the predicted neo-antigens being subclonal (FIG. 2A, C).

Figure 2C:
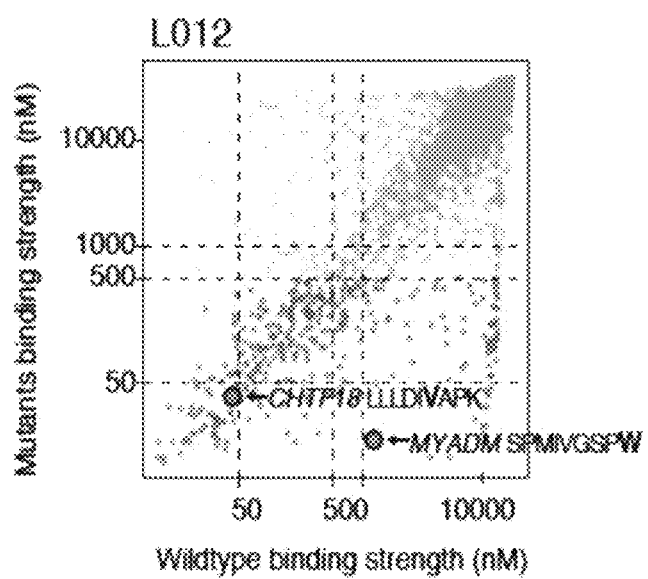
Figure 2D:
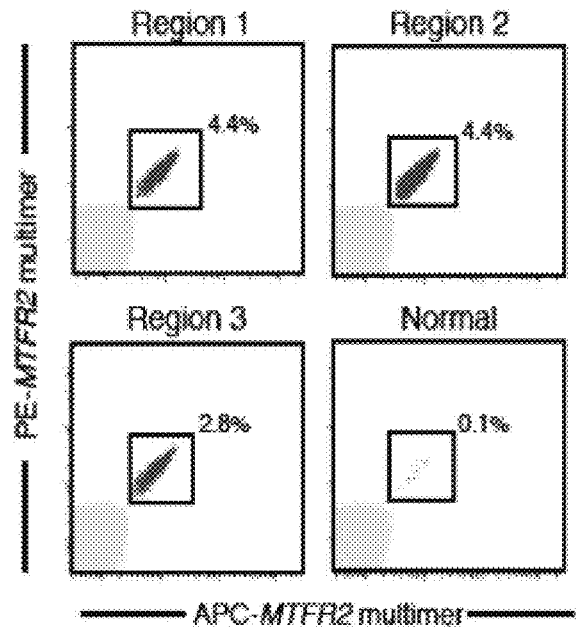
Figure 2E:
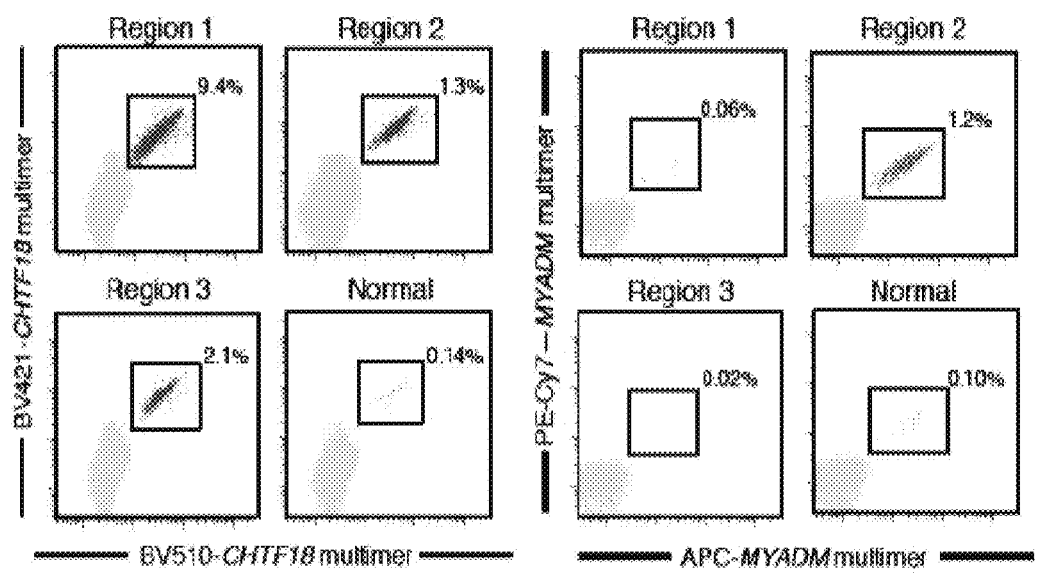

MHC-multimers loaded with predicted neo-antigens were used to screen CD8+ T cells expanded from different tumour regions and adjacent normal lung tissue (13). In L011, CD8+ T cells reactive to mutant MTFR2D326Y (FAFQE YDSF), a clonal mutation with high predicted HLA binding in wild type (10 nM) and mutant (22 nM) forms (FIG. 2B), were identified in all tumour regions (2.8-4.4%) and at lower frequency in normal regions (0.1%) (FIG. 2D). In L012, CD8+ T cells reactive to mutant CHTF18L769V (LLDI VAPK) and MYADMR30W (SPMIVGSP W) were identified in all tumour regions and at lower frequencies in normal tissue (FIG. 2E). Both were clonal mutations, CHTF18 with high predicted HLA binding (<50 nM) in mutant and wild type forms, and MYADM with lower predicted binding in wild type (>1000 nM) compared to mutant form (<50 nM) (FIG. 2C).

Figure 3A:
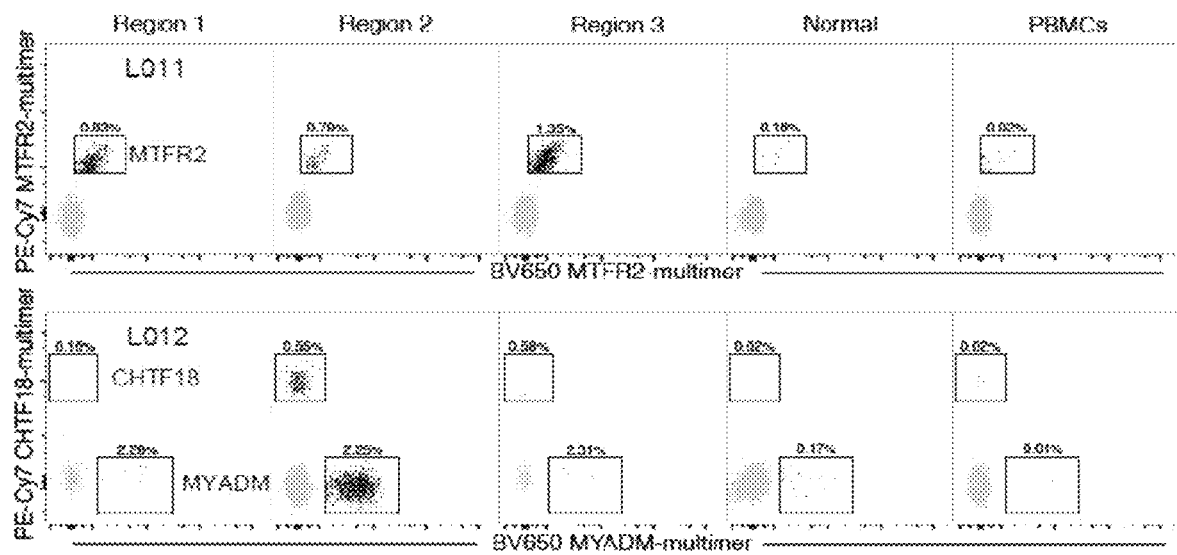
FIGS. 3A-FIG. 3D.

In L011, MTFR2-reactive CD8+ T cells could also be detected in non-expanded TILs (tumour infiltrating lymphocytes) (FIG. 3A) from all primary tumour regions (0.79-1.35%), and at lower frequencies in normal tissue (0.16%) and peripheral blood mononuclear cells (PBMCs) (0.02%). Similarly, CHTF18-reactive and MYADM-reactive CD8+ T cells were identified in non-expanded samples from all tumour regions in L012 (CHTF18 0.16-0.58%, MYADM 2.25-2.31%) and at a lower frequency in normal lung tissue (CHTF18 0.02%, MYADM 0.17%) and PBMCs (CHTF18 0.02%, MYADM 0.01%) (FIG. 3A).

Figure 3B:
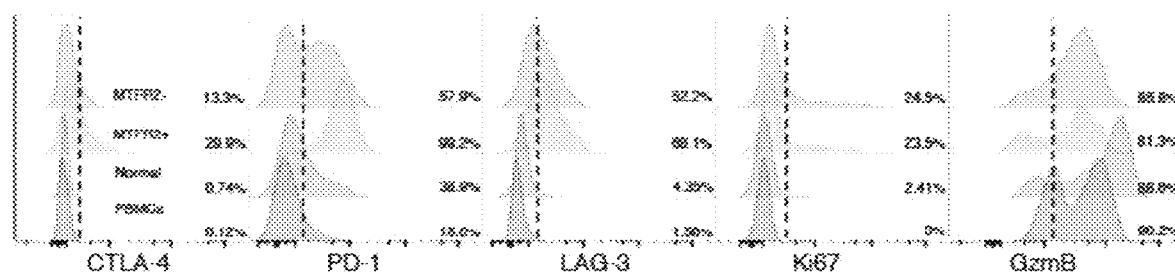
Figure 3C:
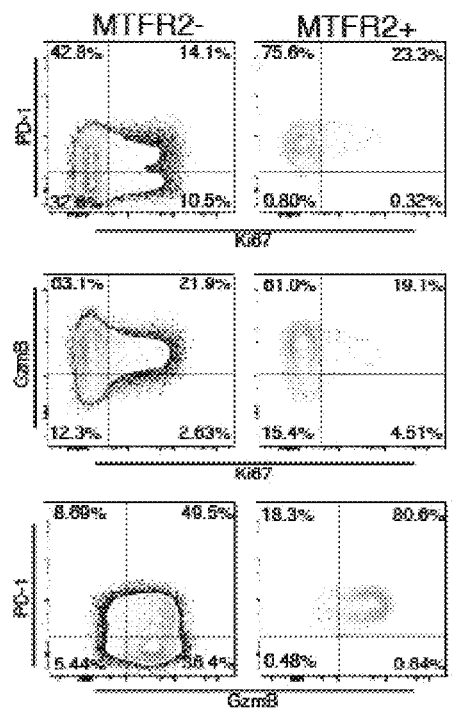
Figure 3D:
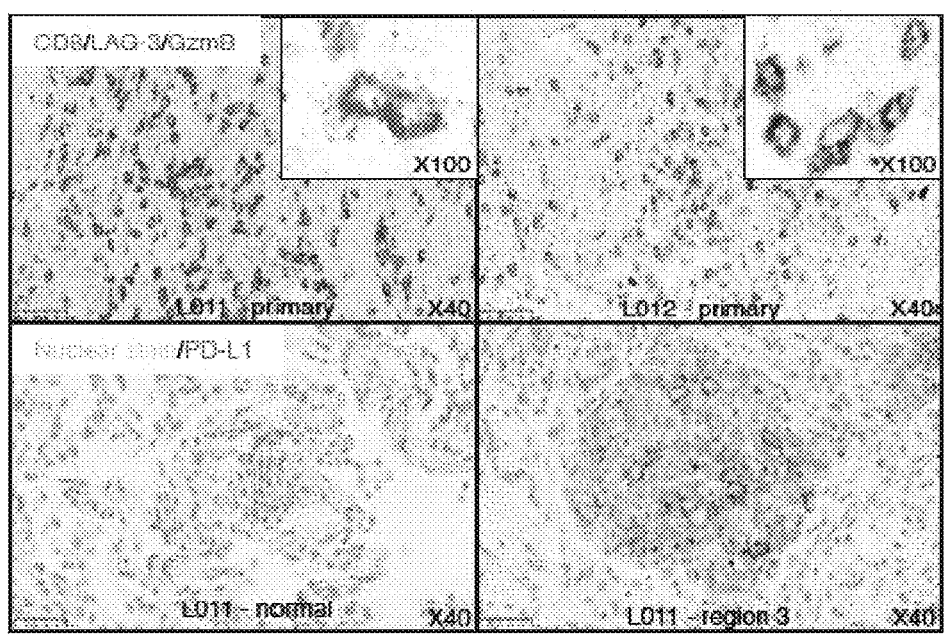

Further characterization of neo-antigen-reactive T cells in non-expanded samples was performed by flow cytometry. Although at low levels, CTLA-4 expression was confined to tumour-infiltrating CD8+ T cells for both L011 and L012, with highest levels identified on MTFR2, CHTF18 and MYADM-reactive T cells (FIG. 3B, FIG. 9A). High levels of PD-1 were expressed by >99% of MTFR2−, CHTF18− and MYADM-reactive tumour-infiltrating CD8+ T cells (FIG. 3B, FIG. 9A), whilst lower levels were observed on CD8+ MHC-multimer negative T cells in tumour, normal tissue and PBMCs. In L011, LAG-3 expression was higher on all tumour rinfiltrating CD8+ T cells, including MTFR2-reactive cells, relative to normal tissue and PBMCs (FIG. 3B). LAG-3 expression was also observed in L012, although at lower levels (FIG. 9A). IHC studies further supported these findings, identifying CD8+ T cells co-expressing LAG-3 in both L011 and L012 primary tumours (FIG. 3D). Ki67 was expressed at higher levels on tumour infiltrating CD8+ T cells than in normal tissue or PBMCs (FIG. 3B, FIG. 9A), however the fraction of proliferating cells was low for both neo-antigen-reactive and MHC-multimer negative cells (<25%). In contrast, granzyme B (GzmB) was expressed at high levels on all studied CD8+ T cell subsets. Importantly, whereas a large proportion of neo-antigen reactive T cells in the tumours appeared highly activated expressing GzmB, the majority of these cells coexpressed PD-1 (>60%) and appeared to be under proliferative control based on Ki67 levels (FIG. 3C, FIG. 9B).

Expression of LAG-3 and PD-1 on T cells reactive to clonal neo-antigens, together with tumour PD-L1 expression (FIG. 3D), strongly supports the immune-signatures identified in high clonal lung tumours (FIG. 1E). These data support a potential role for these specific checkpoints in restricting the activity of T cells recognizing clonal neo-antigens and future studies targeting these checkpoints in NSCLC with high clonal neo-antigen burden.

Figure 10A:
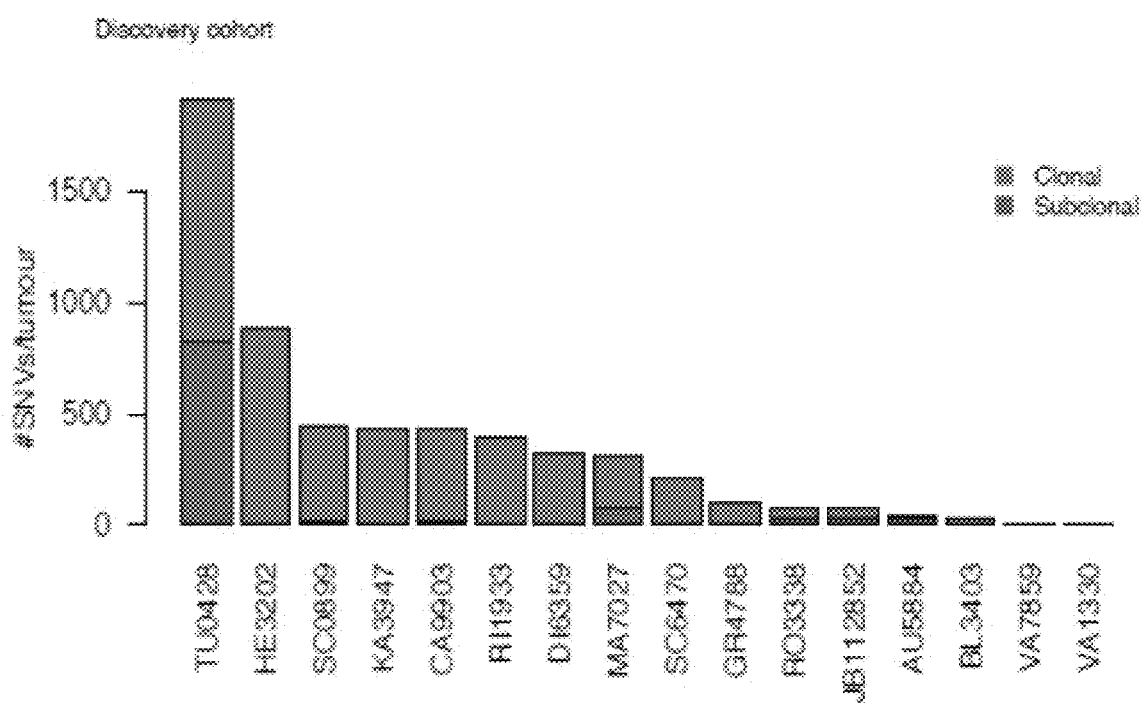
FIGS. 10A-FIG. 10B: Mutational burden and clonal architecture of (FIG. 10A) discovery and (FIG. 10B) validation cohort tumours.
Figure 10B:
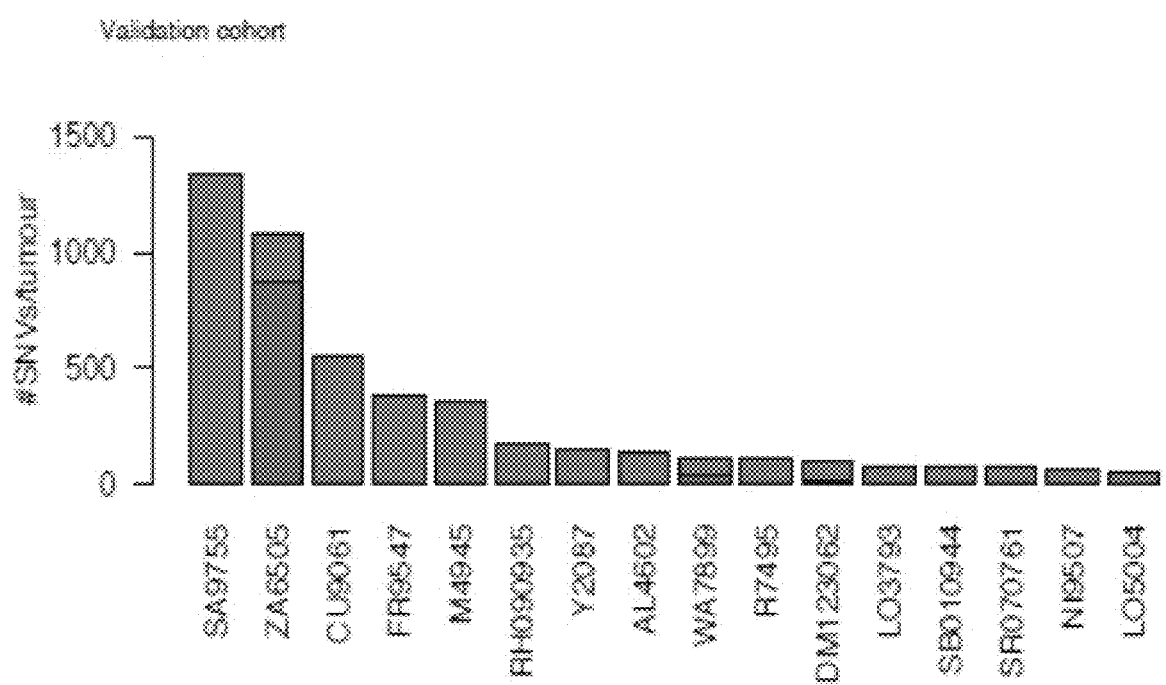

Next, it was explored whether the clonal status of putative neo-antigens might be associated with altered sensitivity to PD-1 blockade in NSCLC. Exome sequencing data from a recent study in which two independent NSCLC cohorts were treated with pembrolizumab was obtained (2)(Table S2), and the clonal architecture of each tumour was dissected by estimating the cancer cell fraction of each mutation (13) (FIGS. 10A-B). As previously reported (2), neo-antigen burden was related to the clinical efficacy of pembrolizumab in the discovery and validation cohort, with a high neo-antigen repertoire associated with improved outcome (data not shown).

Figure 4A:
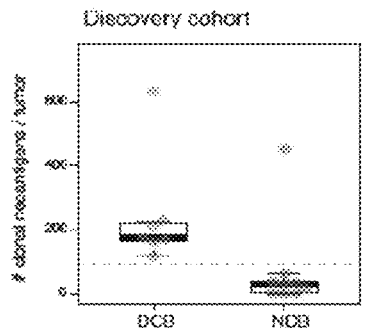
FIGS. 4A-FIG. 4J: For discovery (FIGS. 4A-4C) and validation cohort (FIGS. 4D-4F), number of clonal neo-antigens and fraction of subclonal neo-antigens is shown for patients with a durable clinical benefit (DCB), or non-durable benefit (NDB). Progression free survival in tumours with a higher number of neo-antigens and low subclonal fraction compared to those with a lower number of neo-antigens or high subclonal fraction is shown for discovery (FIG. 4C) and validation (FIG. 4F) cohorts.
Figure 4B:
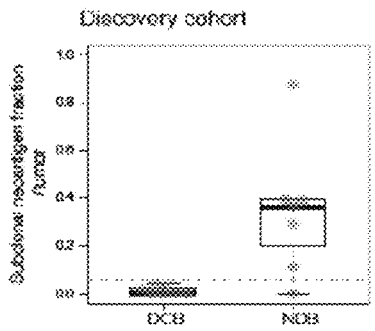
Figure 4C:
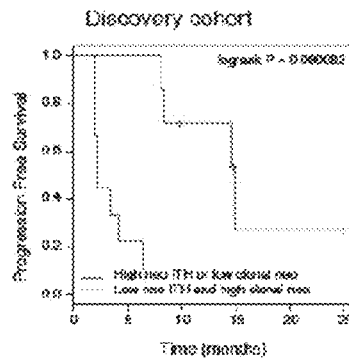
Figure 4D:
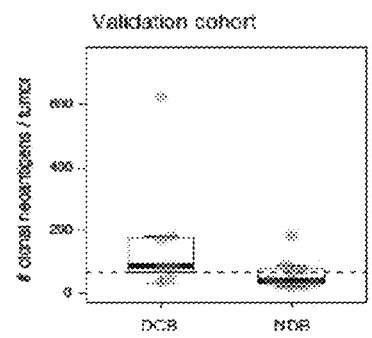
Figure 4E:
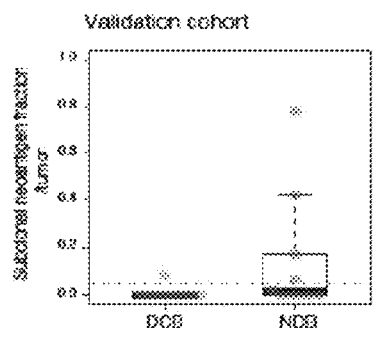
Figure 4F:
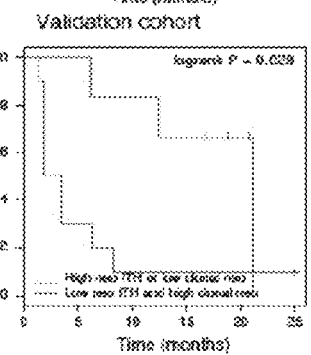
Figure 4G:
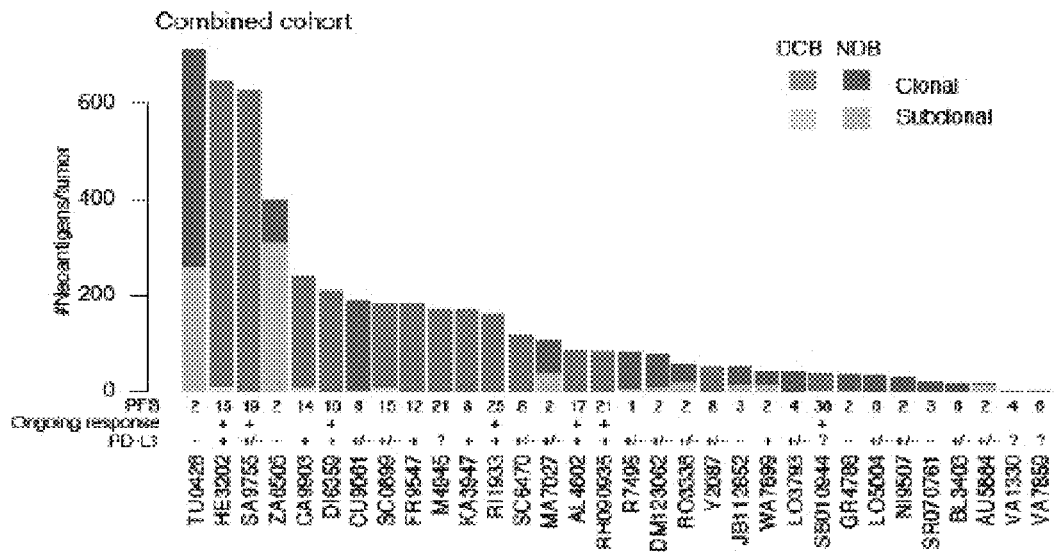
Figure 4H:
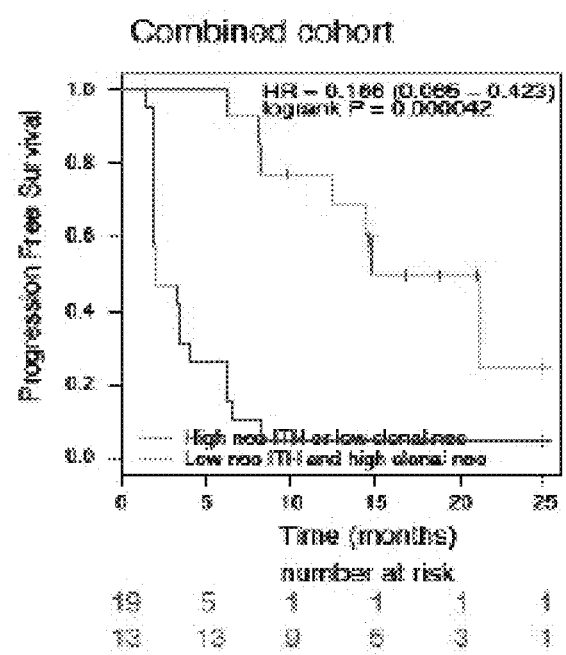

The relationship was also contingent upon the clonal architecture of each tumour (FIG. 4A-H). In the discovery cohort, every tumour exhibiting durable clinical benefit (DCB, defined as in (2) as partial response or stable disease lasting >6 months) harbored a high clonal neo-antigen burden (defined as above or equal to the median number of clonal neo-antigens in the discovery cohort, 91) and a neo-antigen subclonal fraction lower than 5% (FIG. 4A-B). Conversely, every tumour exhibiting a non-durable benefit (NDB) harbored either a low clonal neo-antigen repertoire (<91) or high neo-antigen subclonal fraction (>5%). Thus, in the discovery cohort, combining both neo-antigen repertoire and neo-antigen heterogeneity (i.e. the ratio of clonal:subclonal neo-antigens or mutations) was able to predict sensitivity to pembrolizumab, better than either measure alone (FIG. 4C).

Similarly, in the validation cohort, five of six tumours with a high clonal neo-antigen burden (defined as greater than or equal to the median of the validation cohort, 69) and low subclonal neo-antigen fraction (<5%) were associated with DCB (FIG. 4D-F). Conversely, eight out of ten tumours with low clonal neo-antigen burdens or high neo-antigen heterogeneity were associated with NDB. For instance, despite a large neo-antigen burden, ZA6505 exhibited a nondurable clinical response, relapsing after 2 months. ZA6505 was one of the most heterogeneous tumours within the cohort, with over 80% of mutations classified as subclonal.

In summary, when the extent of neo-antigen heterogeneity and the clonal neo-antigen burden were considered together, outcome could be predicted in almost all cases (FIG. 4G-H).

Figure 4I:
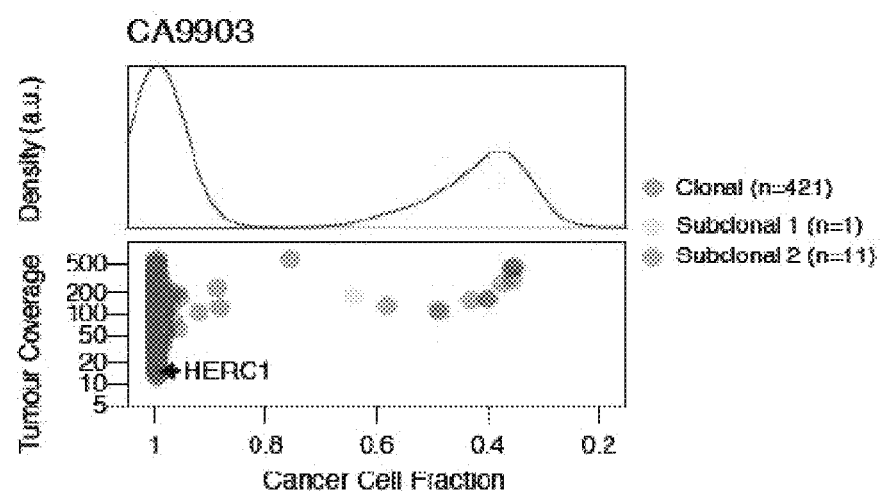
Figure 4J:
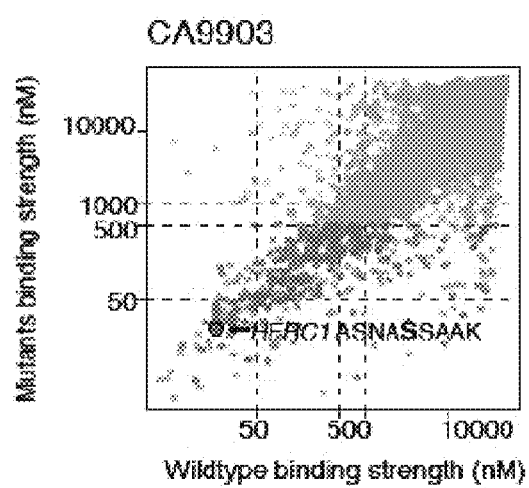
Figure 11:
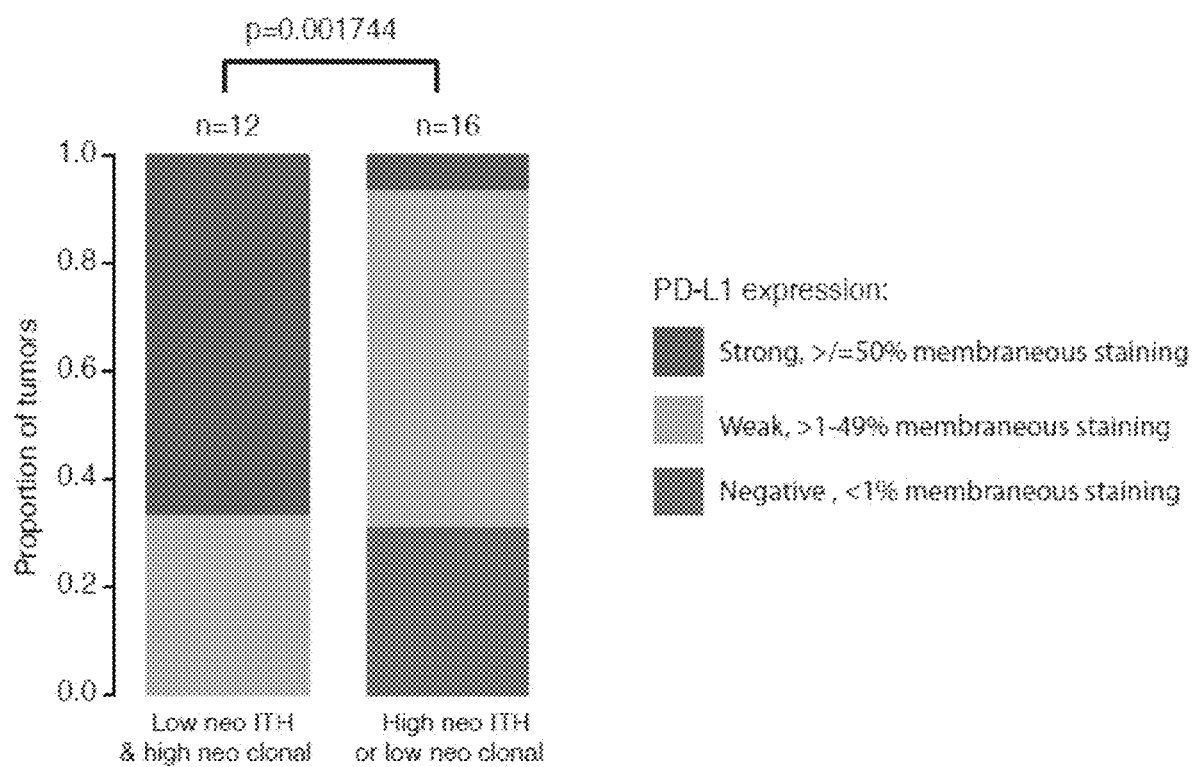
FIG. 11: PD-L1 expression for two groups of tumours. PD-L1 exhibits significantly stronger expression in tumours harboring a high clonal neo-antigen burden and a low subclonal neo-antigen fraction compared to tumours harboring a low clonal neo-antigen burden or high subclonal neo-antigen fraction.
Figure 12A:
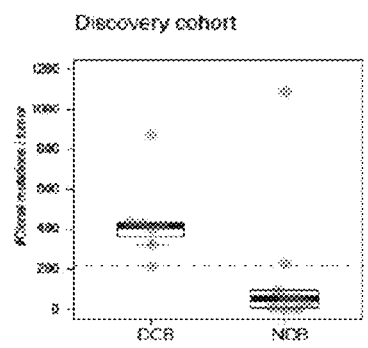
FIGS. 12A-FIG. 12H.
Figure 12B:
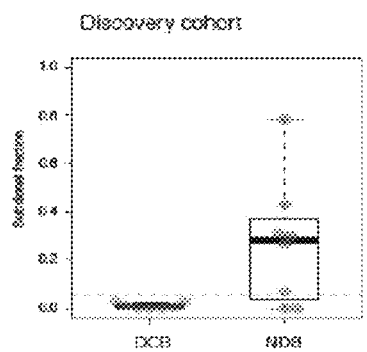
Figure 12C:
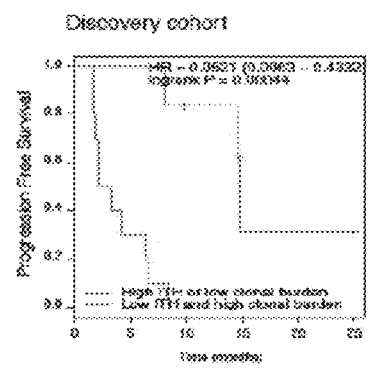
Figure 12D:
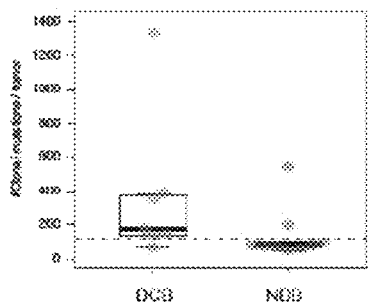
Figure 12E:
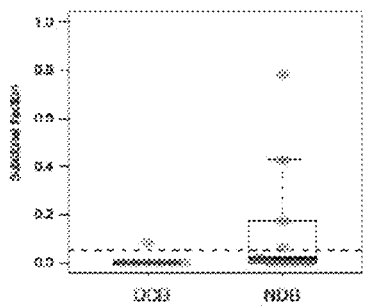
Figure 12F:
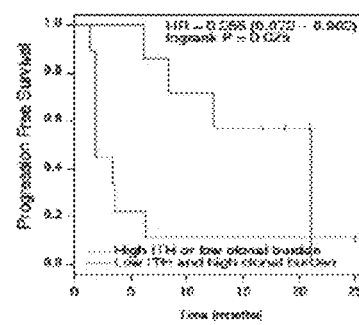
Figure 12G:
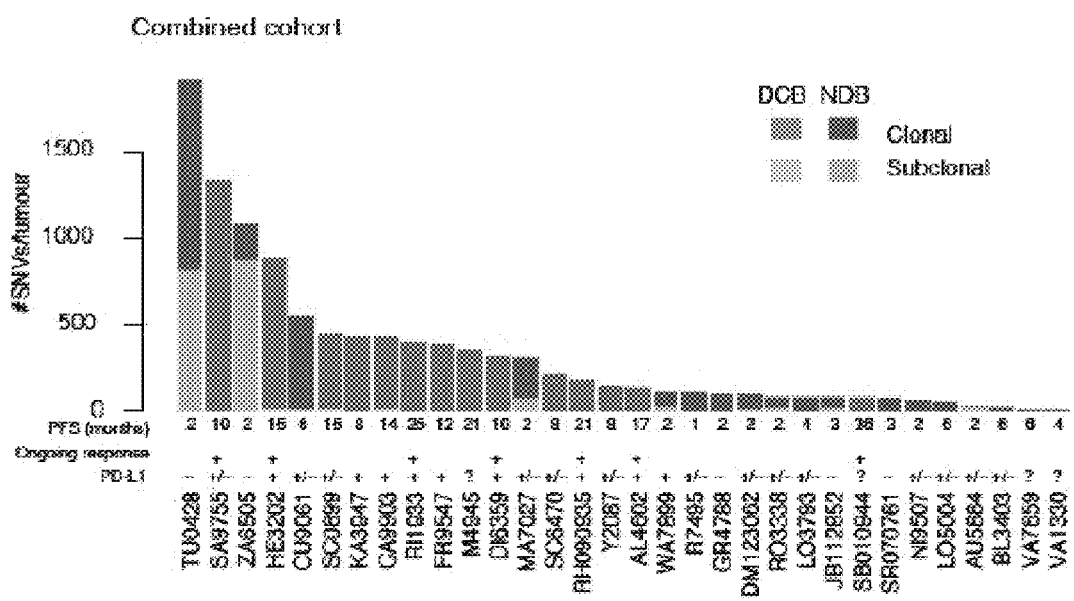
Figure 12H:
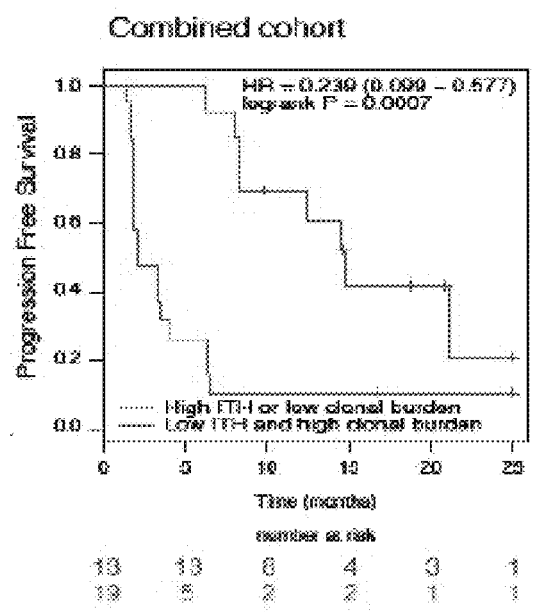

Moreover, in keeping with TOGA analysis (FIG. 1E), we also observed greater PD-L1 expression in tumours harboring a large clonal neo-antigen burden and low neo-antigen heterogeneity compared to those with a low neo-antigen load or high neo-antigen heterogeneity (P=0.0017, x2-test, FIG. 11). These results remained consistent when considering all mutations rather than class-I restricted putative neo-antigens (FIGS. 12A-H), supporting the notion that unidentified MHC class II restricted neo-antigens may also play a significant role in immune reactivity (6) and the need for refinement of neo-antigen prediction algorithms (16), responding to anti-PD-1 therapy. Previous analysis of peripheral blood lymphocytes (PBLs) from CA9903, a tumour with exceptional response to pembrolizumab, identified a CD8+ T cell population in autologous PBLs recognizing a predicted neo-antigen resulting from a HERC1P3278S mutation (ASNASSAAK) (2). Consistent with the relevance of clonal neo-antigens, this mutation was likely present in 100% of cancer cells within the sequenced tumour (FIG. 4I-J).

Supplementary Table S1: Differentially expressed immune genes between high and low clonal neo-antigen patient groups

|  | Mean | log2 Fold Change | p-value | adjusted p-value |
| --- | --- | --- | --- | --- |
| GZMB | 445.7851333 | −1.78462652 | 1.18E−09 | 1.69E−07 |
| TNFSF13 | 3532.313186 | 0.825249238 | 6.24E−08 | 4.13E−06 |
| IL6 | 448.0627177 | −1.816113115 | 1.13E−07 | 6.70E−06 |
| TMEM173 | 3740.991274 | 0.924504705 | 7.26E−07 | 2.84E−05 |
| IFNG | 36.80074093 | −1.756035642 | 8.98E−06 | 0.000202975 |
| PD-L1 | 384.7156773 | −1.42730081 | 1.44E−05 | 0.00029375 |
| CXCL9 | 4559.513492 | −1.511142807 | 1.50E−05 | 0.000302565 |
| STAT1 | 17028.82171 | −0.784356172 | 2.16E−05 | 0.000401426 |
| LAG3 | 277.7770415 | −1.129050218 | 2.51E−05 | 0.000454562 |
| RORA | 634.8938186 | 0.738052259 | 6.53E−05 | 0.000963038 |
| PRDM1 | 1236.570377 | −0.678822885 | 7.91E−05 | 0.001116763 |
| TAP1 | 10724.07983 | −0.763792013 | 0.000338393 | 0.003482612 |
| GNLY | 357.1056535 | −1.047292568 | 0.000560104 | 0.005132755 |
| CXCL10 | 2068.038219 | −1.15715645 | 0.000568625 | 0.005180037 |
| CD8A | 788.7253219 | −0.945122724 | 0.000589072 | 0.005306952 |
| CSF3 | 49.20726456 | −1.359216439 | 0.000907102 | 0.007361937 |
| TBX21 | 76.56429476 | −1.021741775 | 0.000939277 | 0.007541139 |
| GZMH | 186.2030449 | −0.979136784 | 0.001007872 | 0.007952958 |
| TAP2 | 4538.140019 | −0.559264738 | 0.001188075 | 0.008964565 |
| PD-L2 | 332.3493386 | −0.771675574 | 0.002964397 | 0.017858103 |
| PVR | 2940.716051 | −0.567512648 | 0.003336494 | 0.019565463 |
| CD70 | 71.58250113 | −1.050709857 | 0.003388254 | 0.019734624 |
| PD1 | 147.129952 | −0.886846385 | 0.003492638 | 0.020231348 |
| VTCN1 | 822.1971729 | 1.238388678 | 0.005797085 | 0.029375393 |
| CHUK | 1499.467613 | −0.303245758 | 0.006444708 | 0.031673895 |
| SOCS2 | 795.7802019 | 0.663903969 | 0.008580641 | 0.039140625 |
| TNFRSF14 | 2676.212113 | 0.359555349 | 0.009918008 | 0.043580894 |
| CD8B | 213.6687071 | −0.734726572 | 0.012492819 | 0.051665805 |
| IL1B | 462.025209 | −0.701631604 | 0.012892938 | 0.052917717 |
| IL12A | 29.20823765 | −0.68364274 | 0.013729832 | 0.055446871 |
| IL12B | 14.43557004 | 0.783016768 | 0.01707779 | 0.065407095 |
| IL2 | 2.444225976 | 0.986346011 | 0.018986691 | 0.070900521 |
| CX3CL1 | 4506.608644 | 0.67426411 | 0.027478555 | 0.092915037 |
| NOS2 | 41.22675253 | −0.68521024 | 0.029626595 | 0.098142202 |
| TNFRSF18 | 360.9297496 | −0.729059895 | 0.029718057 | 0.098354315 |
| KLRK1 | 182.5573646 | −0.643726062 | 0.030255564 | 0.099453935 |
| MADCAM1 | 7.273228749 | −0.784565543 | 0.048684055 | 0.140368258 |
| GZMA | 578.3953638 | −0.635858589 | 0.050652532 | 0.144348847 |
| VEGFA | 10928.73621 | −0.451684004 | 0.056171355 | 0.155239718 |
| PRF1 | 618.5783468 | −0.473152277 | 0.058353066 | 0.159377477 |
| LGALS9 | 5310.012377 | 0.422760767 | 0.05909457 | 0.160839147 |
| IL7 | 207.9545877 | 0.496316279 | 0.061102723 | 0.164605503 |
| PTGS2 | 6159.88191 | −0.747090631 | 0.063658001 | 0.169174461 |
| TNFRSF4 | 197.5157825 | −0.379177736 | 0.07230099 | 0.184487923 |
| CD160 | 25.1062924 | −0.460251517 | 0.074003068 | 0.187576278 |
| TNFRSF13B | 38.64965649 | 0.578468093 | 0.077739763 | 0.194381934 |
| TIGIT | 239.3616733 | −0.479398507 | 0.079715132 | 0.19772176 |
| TNFRSF9 | 107.0383741 | −0.538183729 | 0.088224384 | 0.211935421 |
| IL8 | 4258.061194 | −0.592100426 | 0.102069566 | 0.234512774 |
| CD86 | 1011.868757 | −0.311180799 | 0.112427315 | 0.250957613 |
| IRF1 | 3898.872307 | −0.322486714 | 0.116076728 | 0.256631346 |

Supplementary Table S1: Differentially expressed immune genes between high and low clonal neo-antigen patient groups

|         | Mean         | log2 Fold Change | p-value     | adjusted p-value |
|---------|--------------|------------------|-------------|------------------|
| CCL5    | 2614.171996  | −0.472610458     | 0.122548084 | 0.266275852      |
| CD28    | 215.0051414  | 0.33366846       | 0.124587781 | 0.26940173       |
| CD200   | 390.5585743  | −0.295026768     | 0.13116523  | 0.27888167       |
| HAVCR2  | 1325.180665  | −0.296647885     | 0.140180116 | 0.291003086      |
| MS4A1   | 390.2558862  | 0.523928974      | 0.15233134  | 0.307579262      |
| IL12RB1 | 198.3081926  | −0.327226759     | 0.161228022 | 0.319922079      |
| TGFB1   | 3705.083958  | −0.203702547     | 0.164951696 | 0.325330473      |
| STAT3   | 14213.7378   | 0.150804216      | 0.169624324 | 0.33151912       |
| CXCR5   | 95.03997316  | 0.416011181      | 0.183763767 | 0.348650978      |
| IDO1    | 1858.956376  | −0.407500734     | 0.23727483  | 0.413799917      |
| CD79A   | 1175.710552  | −0.341052525     | 0.263424151 | 0.443401388      |
| IL10RB  | 3285.337481  | 0.152074186      | 0.292309086 | 0.475665005      |
| IRF5    | 980.613802   | −0.193865677     | 0.294881352 | 0.478239401      |
| CXCR3   | 271.2315304  | −0.283719077     | 0.29632793  | 0.479863349      |
| TNFSF9  | 294.2710962  | −0.291633453     | 0.298080985 | 0.481806159      |
| NR4A1   | 4233.840543  | 0.308559097      | 0.307663118 | 0.491861702      |
| CD69    | 636.205301   | 0.310698903      | 0.313829669 | 0.498082357      |
| TNFRSF13C | 23.54714796 | −0.27661096      | 0.320174619 | 0.504889662      |
| CTLA4   | 144.1973513  | −0.252213052     | 0.337165917 | 0.523370695      |
| CD80    | 118.3959403  | −0.219168442     | 0.344168801 | 0.531186145      |
| VEGFB   | 3813.436412  | 0.111428746      | 0.348255092 | 0.535082065      |
| CD276   | 4839.942708  | −0.110880457     | 0.354884606 | 0.541381686      |
| TNFSF4  | 285.0994787  | −0.251740957     | 0.367394794 | 0.552571633      |
| IL15    | 251.954005   | −0.227790082     | 0.372118713 | 0.557431842      |
| HLA-B   | 117419.6406  | −0.189404462     | 0.392700995 | 0.577313935      |
| TNFSF18 | 10.50871731  | 0.278307077      | 0.434127114 | 0.615308001      |
| CSF2    | 82.00905002  | 0.258772851      | 0.456961522 | 0.635760218      |
| IKBKB   | 3029.277618  | 0.123880242      | 0.462066231 | 0.639685204      |
| HLA-E   | 28263.91252  | 0.112748395      | 0.463864656 | 0.641508215      |
| CD3D    | 468.5251485  | −0.215789423     | 0.464458271 | 0.642153767      |
| EOMES   | 73.96153664  | −0.207485464     | 0.471039076 | 0.647525273      |
| LTA     | 47.75821054  | 0.202745276      | 0.48236162  | 0.656627117      |
| CD244   | 84.89011319  | −0.186732614     | 0.494820217 | 0.667103087      |
| HLA-C   | 76083.94895  | −0.133189426     | 0.505495645 | 0.676055645      |
| TGFBR1  | 3202.195003  | −0.08370058      | 0.506750828 | 0.677080529      |
| CXCL5   | 944.0905877  | −0.270235841     | 0.521955968 | 0.689704336      |
| HLA-G   | 411.9342955  | 0.179225426      | 0.52944301  | 0.695460893      |
| TGFB3   | 950.0375094  | −0.121079367     | 0.553603166 | 0.71443979       |
| B2M     | 172378.9968  | 0.110580042      | 0.561947299 | 0.72111769       |
| ICAM1   | 22061.71601  | −0.143421343     | 0.563916412 | 0.722858104      |
| CD40    | 1772.030076  | −0.119567048     | 0.600081755 | 0.750332383      |
| IL10    | 48.9483278   | −0.143330001     | 0.611619228 | 0.759687642      |
| CD3E    | 926.6666625  | −0.132795883     | 0.613950098 | 0.761354179      |
| HLA-F   | 6351.352815  | 0.120347259      | 0.628199687 | 0.771810162      |
| VCAM1   | 2159.418805  | −0.130117222     | 0.642682858 | 0.782745807      |
| CD79B   | 343.535879   | 0.127051943      | 0.65365394  | 0.790469331      |
| CCL2    | 2809.121226  | 0.112856687      | 0.682702276 | 0.810562013      |
| FOXP3   | 194.391431   | 0.111548571      | 0.689381473 | 0.815575495      |
| BTLA    | 62.23164316  | −0.102004115     | 0.732037222 | 0.845834192      |
| SOCS1   | 433.4195773  | 0.082676919      | 0.734857322 | 0.84806292       |
| CD2     | 948.4310392  | −0.086505902     | 0.742632845 | 0.85329242       |
| CD3G    | 131.2700215  | −0.09041107      | 0.743838306 | 0.853911324      |
| CXCL13  | 1506.896218  | −0.118364398     | 0.755758076 | 0.861471947      |
| ICOS    | 120.5538816  | −0.086753989     | 0.760044117 | 0.864093608      |
| CXCL1   | 960.6911493  | 0.085909113      | 0.800874166 | 0.889816067      |
| CD4     | 5270.88003   | −0.045153828     | 0.813688182 | 0.898429619      |
| BCL6    | 2893.728602  | −0.030670947     | 0.831857609 | 0.909937895      |
| IL1A    | 52.50184149  | −0.071209064     | 0.835686639 | 0.912278655      |
| CD19    | 119.1478854  | −0.060259488     | 0.8618787   | 0.926697933      |
| HLA-A   | 92787.6356   | −0.033095882     | 0.871822173 | 0.932461535      |
| CD38    | 401.6927917  | 0.038510446      | 0.899895838 | 0.945971695      |
| CD27    | 637.0929506  | −0.02998534      | 0.908371198 | 0.951425293      |
| STAT5A  | 1460.392543  | 0.003525758      | 0.977657023 | 0.99064235       |
| IKBKG   | 1236.266327  | 0.002038592      | 0.989162825 | 0.995429737      |
| ARG1    | 1.115682528  | −0.318253465     | 0.491866502 | NA               |
| IL21    | 0.790890355  | −1.092615876     | 0.040972459 | NA               |
| IL4     | 0.54010078   | 0.784036263      | 0.143480734 | NA               |

SUPPLEMENTARY TABLE S2

| | | Detailed clinical characteristics of individual patients | | | | | | |
|---|---|---|---|---|---|---|---|---|
| # | Study ID | Cohort (Discovery, Validation) | Histology | Age (years) | Sex | Smok.^ | Pack-years | PD-L1* |
| 1 | SA9755 | Valid | NSCLC NOS | 63 | F | Former | 36 | Weak |
| 2 | HE3202 | Disc | Adeno | 63 | F | Former | 58 | Strong |
| 3 | TU0428 | Disc | Adeno | 66 | M | Current | 48 | Negative |
| 4 | Y2087 | Valid | Adeno | 68 | F | Never | 0 | Weak |
| 5 | M4945 | Valid | Adeno | 66 | M | Former | 40 | Unknown |
| 6 | RI1933 | Disc | Adeno | 60 | F | Former | 21 | Strong |
| 7 | ZA6505 | Valid | Adeno | 76 | F | Never | 0 | Negative |
| 8 | CU9061 | Valid | Squam | 57 | M | Former | 39 | Weak |
| 9 | CA9903 | Disc | Adeno | 57 | M | Former | 80 | Strong |
| 10 | SC0899 | Disc | Adeno | 64 | F | Current | 25 | Weak |
| 11 | FR9547 | Valid | Adeno | 65 | F | Current | 25 | Strong |
| 12 | KA3947 | Disc | Adeno | 64 | F | Former | 52.5 | Strong |
| 13 | MA7027 | Disc | Adeno | 56 | M | Former | 37.5 | Weak |
| 14 | ZA6965 | Valid | Adeno | 57 | F | Former | 25 | Strong |
| 15 | AL4602 | Valid | Adeno | 59 | M | Former | 34 | Strong |
| 16 | JB112852 | Disc | Adeno | 60 | M | Never | 0 | Negative |
| 17 | SR070761 | Valid | Squam | 51 | F | Former | 2.5 | Negative |
| 18 | DI6359 | Disc | Adeno | 61 | F | Current | 60 | Strong |
| 19 | SB010944 | Valid | Squam | 68 | M | Never | 0 | Unknown |
| 20 | RH090935 | Valid | Adeno | 78 | F | Former | 60 | Strong |
| 21 | SC6470 | Disc | Adeno | 59 | M | Current | 15 | Weak |
| 22 | BL3403 | Disc | Adeno | 73 | F | Former | 43.75 | Weak |
| 23 | GR4788 | Disc | Squam | 59 | M | Current | 45 | Negative |
| 24 | DM123062 | Valid | Adeno | 50 | M | Never | 0 | Weak |
| 25 | R7495 | Valid | Adeno | 63 | M | Former | 73.5 | Weak |
| 26 | WA7899 | Valid | Adeno | 49 | M | Never | 0 | Strong |
| 27 | RO3338 | Disc | Adeno | 71 | M | Former | 20 | Weak |
| 28 | LO3793 | Valid | Adeno | 62 | F | Former | 6 | Weak |
| 29 | LO5004 | Valid | Adeno | 56 | F | Former | 8 | Weak |
| 30 | GR0134 | Valid | Adeno | 80 | M | Former | 56 | Negative |
| 31 | VA1330 | Disc | Adeno | 71 | F | Former | 0.5 | Unknown |
| 32 | NI9507 | Valid | Adeno | 41 | F | Current | 2.25 | Weak |
| 33 | AU5884 | Disc | Adeno | 64 | M | Former | 10 | Weak |
| 34 | VA7859 | Disc | Adeno | 57 | F | Former | 3.15 | Unknown |

| # | Priors^^ | Dose (mg/kg) | Sched.** | PFS (mos) | Event^^^ | Resp^^^ | Durable Clinical Benefit |
|---|---|---|---|---|---|---|---|
| 1 | 1 | 10 | 3 | 18.8 | 0 | PR | DCB |
| 2 | 3 | 10 | 3 | 14.7 | 0 | PR | DCB |
| 3 | 0 | 10 | 3 | 2.1 | 1 | POD | NDB |
| 4 | 5 | 10 | 3 | 8.3 | 1 | SD | DCB |
| 5 | 3 | 10 | 2 | 21.1 | 1 | PR | DCB |
| 6 | 1 | 10 | 3 | 25.2 | 0 | PR | DCB |
| 7 | 6 | 10 | 3 | 1.9 | 1 | POD | NDB |
| 8 | 1 | 2 | 3 | 6.2 | 1 | SD | NDB |
| 9 | 3 | 10 | 3 | 14.5 | 1 | PR | DCB |
| 10 | 0 | 10 | 3 | 14.8 | 1 | PR | DCB |
| 11 | 1 | 2 | 3 | 12.4 | 1 | PR | DCB |
| 12 | 0 | 10 | 3 | 8.1 | 1 | SD | DCB |
| 13 | 1 | 10 | 2 | 1.8 | 1 | POD | NDB |
| 14 | 1 | 2 | 3 | 14.5 | 0 | PR | DCB |
| 15 | 0 | 10 | 3 | 16.8 | 0 | SD | DCB |
| 16 | 5 | 10 | 2 | 3.3 | 1 | POD | NDB |
| 17 | 4 | 10 | 2 | 3.4 | 1 | POD | NDB |
| 18 | 6 | 10 | 3 | 9.8 | 0 | PR | DCB |
| 19 | 2 | 10 | 3 | 35.7 | 0 | PR | DCB |
| 20 | 0 | 10 | 3 | 20.9 | 0 | PR | DCB |
| 21 | 0 | 10 | 2 | 8.3 | 1 | SD | DCB |
| 22 | 1 | 10 | 2 | 6.5 | 1 | SD | NDB |
| 23 | 0 | 10 | 2 | 1.9 | 1 | POD | NDB |
| 24 | 6 | 10 | 2 | 1.9 | 1 | POD | NDB |
| 25 | 2 | 2 | 3 | 1.4 | 1 | POD | NDB |
| 26 | 2 | 10 | 3 | 1.9 | 1 | POD | NDB |
| 27 | 1 | 10 | 3 | 2.1 | 1 | POD | NDB |
| 28 | 2 | 2 | 3 | 3.5 | 1 | SD | NDB |
| 29 | 0 | 10 | 2 | 6.3 | 1 | SD | NDB |
| 30 | 0 | 10 | 3 | 8.3 | 1 | PR | DCB |
| 31 | 1 | 10 | 3 | 4.1 | 1 | SD | NDB |
| 32 | 1 | 10 | 3 | 1.9 | 1 | POD | NDB |

SUPPLEMENTARY TABLE S2-continued

Detailed clinical characteristics of individual patients

| | | | | | | | | |
|---|---|---|---|---|---|---|---|---|
| 33 | 2 | 10 | 2 | 1.8 | 1 | POD | NDB |
| 34 | 1 | 10 | 3 | 6.3 | 1 | SD | NDB |

\#, patient number.
Adeno, adenocarcinoma.
Squam, squamous cell carcinoma.
NSCLC NOS, non small-cell lung cancer, not otherwise specified. PFS, progression free survival.
\*\*Pembrolizumab dosed every 2 or 3 weeks as indicated.
\*PDL-1 expression. Strong, >/=50% membraneous staining; Weak, 1-49% membraneous staining; Negative, <1% membraneous staining; Unknown, unassessable
^^^^Resp. denotes best overall response to pembrolizumab.
^^^Event (1) or censure (0) for progression-free survival
^^Prior courses of cytotoxic chemotherapy. Combination chemotherapy counted as a single course. No patient had received prior immunotherapy.
^Self-reported smoking status.
DCB, durable clinical benefit beyond 6 months.
NDB, no durable benefit.
NR, not reached 6 months follow-up.
F, Female.
M, Male.
P, positive.
No, negative.
U, unknown.
Smok., Smoking status.
Pack-years, product of number of packs per day and number of years smoked.
Sched., Schedule of administration in weeks.
Mos, months.
Resp., best overall response.

References

1. N. A. Rizvi et al., Cancer immunology. Mutational landscape determines sensitivity to PD-1 blockade in non-small cell lung cancer. *Science* (New York, N.Y. 348, 124-128 (2015).

2. M. S. Lawrence et al., Discovery and saturation analysis of cancer genes across 21 tumour types. *Nature* 505, 495-501 (2014).

3. M. Gerlinger et al., Genomic architecture and evolution of clear cell renal cell carcinomas defined by multiregion sequencing. *Nature genetics* 46, 225-233 (2014).

4. M. Gerlinger et al., Intratumour heterogeneity and branched evolution revealed by multiregion sequencing. *The New England journal of medicine* 366, 883-892 (2012).

5. A. McKenna et al., The Genome Analysis Toolkit: a MapReduce framework for analyzing next-generation DNA sequencing data. *Genome research* 20, 1297-1303 (2010).

6. H. Li, R. Durbin, Fast and accurate short read alignment with Burrows-Wheeler transform. *Bioinformatics* 25, 1754-1760 (2009).

7. H. Li et al., The Sequence Alignment/Map format and SAMtools. *Bioinformatics* 25, 2078-2079 (2009).

8. D. C. Koboldt et al., VarScan 2: somatic mutation and copy number alteration discovery in cancer by exome sequencing. *Genome research* 22, 568-576 (2012).

9. J. T. Robinson et al., Integrative genomics viewer. *Nature biotechnology* 29, 24-26 (2011).

10. K. Nakamura et al., Sequence-specific error profile of Illumina sequencers. *Nucleic Acids Res* 39, e90 (2011).

11. K. Wang, M. Li, H. Hakonarson, ANNOVAR: functional annotation of genetic variants from high-throughput sequencing data. *Nucleic Acids Res* 38, e164 (2010).

12. N. Murugaesu et al., Tracking the genomic evolution of esophageal adenocarcinoma through neoadjuvant chemotherapy. *Cancer discovery*, (2015).

13. E. C. de Bruin et al., Spatial and temporal diversity in genomic instability processes defines lung cancer evolution. *Science* (New York, N.Y. 346, 251-256 (2014).

14. N. McGranahan et al., Clonal status of actionable driver events and the timing of mutational processes in cancer evolution. *Sci Transl Med* 7, 283ra254 (2015).

15. C. L. Hodgkinson et al., Tumourigenicity and genetic profiling of circulating tumour cells in small-cell lung cancer. *Nature medicine* 20, 897-903 (2014).

16. S. A. Shukla et al., Comprehensive analysis of cancer-associated somatic mutations in class I HLA genes. *Nature biotechnology*, (In press). 17. A. Szolek et al., OptiType: precision HLA typing from next-generation sequencing data. Bioinformatics 30, 3310-3316 (2014).

18. I. Hoof et al., NetMHCpan, a method for MHC class I binding prediction beyond humans. *Immunogenetics* 61, 1-13 (2009).

19. M. Nielsen et aL, NetMHCpan, a method for quantitative predictions of peptide binding to any HLA-A and -B locus protein of known sequence. *PloS one* 2, e796 (2007).

20. M. Toebes et aL, Design and use of conditional MHC class I ligands. *Nature medicine* 12, 246-251 (2006).

21. A. H. Bakker et aL, Conditional MHC class I ligands and peptide exchange technology for the human MHC gene products HLA-A1, -A3, -A11, and -B7. *Proceedings of the National Academy of Sciences of the United States of America* 105, 3825-3830 (2008).

22. T. M. Frosig et aL, Design and validation of conditional ligands for HLAB*08:01, HLA-B*15:01, HLA-B*35:01, and HLA-B*44:05. *Cytometry A*, (2015).

23. C. X. Chang et aL, Conditional ligands for Asian HLA variants facilitate the definition of CD8+ T-cell responses in acute and chronic viral diseases. *Eur J Immunol* 43, 1109-1120 (2013).

24. S. R. Hadrup et aL, Parallel detection of antigen-specific T-cell responses by multidimensional encoding of MHC multimers. *Nat Methods* 6, 520-526 (2009).

25. R. S. Andersen et aL, Parallel detection of antigen-specific T cell responses by combinatorial encoding of MHC multimers. *Nature protocols* 7, 891-902 (2012).

26. T. Marafioti et aL, Novel markers of normal and neoplastic human plasmacytoid dendritic cells. *Blood* 111, 3778-3792 (2008).

27. A. U. Akarca et aL, BRAF V600E mutation-specific antibody, a sensitive diagnostic marker revealing minimal residual disease in hairy cell leukaemia. *Br J Haematol* 162, 848-851 (2013).

28. T. Marafioti et aL, Phenotype and genotype of inter-follicular large B cells, a subpopulation of lymphocytes often with dendritic morphology. *Blood* 102, 2868-2876 (2003).

All documents referred to herein are hereby incorporated by reference in their entirety, with special attention to the subject matter for which they are referred Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A method of treating cancer in a subject, wherein said method comprises the following steps:
   (a) identifying a subject with cancer who is suitable for treatment with an immune checkpoint intervention by:
      (i) determining the number of clonal neo-antigens in one or more cancer cells from said subject; and/or
      (ii) determining the ratio of clonal:sub-clonal neoantigens and/or sub-clonal neoantigen fraction in more than one cancer cell from said subject;
   (b) detecting a higher number of clonal neoantigens, and/or a higher ratio of clonal:sub-clonal neoantigens, or lower sub-clonal neoantigen fraction, in comparison to a reference sample; and
   (c) treating said subject with an immune checkpoint intervention that comprises an immune checkpoint inhibitor antibody.

2. The method according to claim 1, wherein the immune checkpoint intervention comprises an immune checkpoint inhibitor antibody that interacts with CTLA4, PD-1, PD-L1, Lag-3, Tim-3, TIGIT or BTLA.

3. The method according to claim 2, wherein the immune checkpoint intervention is pembrolizumab, nivolumab, atezolizumab or ipilimumab.

4. The method according to claim 1, wherein the cancer is selected from bladder cancer, gastric cancer, oesophageal cancer, breast cancer, colorectal cancer, cervical cancer, ovarian cancer, endometrial cancer, kidney cancer, lung cancer, brain cancer, melanoma, lymphoma, small bowel cancers, leukemia, pancreatic cancer, hepatobiliary tumours, germ cell cancers, prostate cancer, head and neck cancers, thyroid cancer and sarcomas.

5. The method according to claim 4, wherein the cancer is lung cancer or melanoma.

6. The method according to claim 5, wherein the cancer is non-small cell lung cancer (NSCLC).

7. The method according to claim 1, wherein the subject is a mammal.

8. The method according to claim 7, wherein the subject is a human.

9. The method according to claim 1,
   wherein steps (a) and (b) further comprise:
   determining the expression profile of immune checkpoint molecules in cancer cells and/or tumour infiltrating immune cells from said subject, or tumour type, and
   detecting differential immune checkpoint molecule expression in the cancer cells and/or the tumour infiltrating immune cells, in comparison to a reference sample.

10. The method according to claim 9, wherein determining the expression profile of immune checkpoint molecules is performed by a transcriptome-wide differential gene expression analysis to identify differentially expressed immune checkpoint-related genes.

11. The method according to claim 1, wherein the immune checkpoint intervention comprises an immune checkpoint inhibitor antibody that interacts with CTLA4, PD-1, or PD-L1.

12. The method according to claim 2, wherein the immune checkpoint intervention is pembrolizumab, nivolumab, atezolizumab or ipilimumab.

13. A method of treating cancer in a subject which comprises treating a subject with cancer with an immune checkpoint intervention, wherein the subject has been determined to have:
    (i) a higher number of clonal neo-antigens; and/or
    (ii) a higher ratio of clonal:sub-clonal neo-antigens, or lower sub-clonal neo-antigen fraction in comparison to a reference sample, and
    wherein the immune checkpoint intervention comprises an immune checkpoint inhibitor antibody.

14. The method according to claim 13, wherein the immune checkpoint intervention comprises an immune checkpoint inhibitor antibody that interacts with CTLA4, PD-1, PD-L1, Lag-3, Tim-3, TIGIT or BTLA.

15. The method according to claim 14, wherein the immune checkpoint intervention is pembrolizumab, nivolumab, atezolizumab or ipilimumab.

16. The method according to claim 13, wherein the subject has further been determined to have a differential immune checkpoint molecule expression in comparison to a reference sample.

17. The method according to claim 16, wherein the expression profile of immune checkpoint molecules has been performed by a transcriptome-wide differential gene expression analysis to identify differentially expressed immune checkpoint-related genes.

18. The method according to claim 13, wherein the cancer is selected from bladder cancer, gastric cancer, oesophageal cancer, breast cancer, colorectal cancer, cervical cancer, ovarian cancer, endometrial cancer, kidney cancer, lung cancer, brain cancer, melanoma, lymphoma, small bowel cancers, leukemia, pancreatic cancer, hepatobiliary tumours, germ cell cancers, prostate cancer, head and neck cancers, thyroid cancer and sarcomas.

19. The method according to claim 18, wherein the cancer is lung cancer or melanoma.

20. The method according to claim 19, wherein the cancer is a non-small cell lung cancer (NSCLC).

21. The method according to claim 13, wherein the subject is a mammal.

22. The method according to claim 21, wherein the subject is a human.

23. The method according to claim 13, wherein the immune checkpoint intervention comprises an immune checkpoint inhibitor antibody that interacts with CTLA4, PD-1, or PD-L1.

24. The method according to claim 13, wherein the immune checkpoint intervention comprises an immune checkpoint inhibitor antibody that interacts with CTLA4, PD-1, or PD-L1.

25. A method of treating cancer with checkpoint inhibitor interventions in a plurality of subjects with cancer in a targeted fashion, wherein said method comprises:
    (a) identifying at least one human subject from a plurality of human subjects with cancer who are suitable for treatment with an immune checkpoint intervention by:
        (i) determining the number of clonal neo-antigens in one or more cancer cells from each of said human subjects; and/or
        (ii) determining the ratio of clonal:sub-clonal neoantigens and/or sub-clonal neoantigen fraction in more than one cancer cell from each of said human subjects;
    (b) detecting a higher number of clonal neoantigens, and/or a higher ratio of clonal:sub-clonal neoantigens, or lower sub-clonal neoantigen fraction, in comparison to a reference sample in the at least one of said human subjects; and
    (c) treating the at least one human subject with the higher number of clonal antigens or the higher ratio of the clonal:sub-clonal neoantigens with an immune checkpoint intervention that comprises an immune checkpoint inhibitor antibody.

* * * * *

UNITED STATES PATENT AND TRADEMARK OFFICE
CERTIFICATE OF CORRECTION

PATENT NO. : 11,098,121 B2
APPLICATION NO. : 15/758165
DATED : August 24, 2021
INVENTOR(S) : Nicholas McGranahan et al.

It is certified that error appears in the above-identified patent and that said Letters Patent is hereby corrected as shown below:

In the Specification

Column 3 Line 41: "TOGA" should be --TCGA--

Column 3 Line 66: "MYADMR3OW" should be --MYADMR30W--

Column 4 Line 64: "TOGA LUSCpatients" should be --TCGA LUSC patients--

Column 4 Line 65: "clonal blue)" should be --clonal (blue)--

Column 21 Line 56: "SPMIVGSP W" should be --SPMIVGSPW--

Column 22 Line 18: "rinfiltrating" should be --infiltrating--

Column 23 Line 18: "TOGA" should be --TCGA--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: MTFR2D326Y neo-antigen

<400> SEQUENCE: 1

Phe Ala Phe Gln Glu Tyr Asp Ser Phe
1               5

<210> SEQ ID NO 2
<211> LENGTH: 9
<212> TYPE: PRT
<213> ORGANISM: Artificial Sequence
<220> FEATURE:
<223> OTHER INFORMATION: CHTF18 L769V neo-antigen

<400> SEQUENCE: 2

Leu Leu Leu Asp Ile Val Ala Pro Lys
1               5

<210> SEQ ID NO 3
<211> LENGTH: 9
<212> TYPE: PRT
<213> ORGANISM: Artificial Sequence
<220> FEATURE:
<223> OTHER INFORMATION: MYADMR30W neo-antigen

<400> SEQUENCE: 3

Ser Pro Met Ile Val Gly Ser Pro Trp
1               5

<210> SEQ ID NO 4
<211> LENGTH: 9
<212> TYPE: PRT
<213> ORGANISM: Artificial Sequence
<220> FEATURE:
<223> OTHER INFORMATION: HERC1P3278S neo-antigen

<400> SEQUENCE: 4

Ala Ser Asn Ala Ser Ser Ala Ala Lys
1               5

<210> SEQ ID NO 5
<211> LENGTH: 9
<212> TYPE: PRT
<213> ORGANISM: Homo sapiens

<400> SEQUENCE: 5

Phe Ala Phe Gln Glu Asp Asp Ser Phe
1               5
```

<210> SEQ ID NO 6
<211> LENGTH: 10
<212> TYPE: PRT
<213> ORGANISM: Artificial Sequence
<220> FEATURE:
<223> OTHER INFORMATION: overlapping peptide sequence

<400> SEQUENCE: 6

Ala Phe Gln Glu Tyr Asp Ser Phe Glu Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: overlapping peptide sequence

<400> SEQUENCE: 7

Lys Phe Ala Phe Gln Glu Tyr Asp Ser Phe
1               5                   10

<210> SEQ ID NO 8
<211> LENGTH: 9
<212> TYPE: PRT
<213> ORGANISM: Homo sapiens

<400> SEQUENCE: 8

Leu Leu Leu Asp Ile Leu Ala Pro Lys
1               5

<210> SEQ ID NO 9
<211> LENGTH: 10
<212> TYPE: PRT
<213> ORGANISM: Artificial Sequence
<220> FEATURE:
<223> OTHER INFORMATION: overlapping peptide sequence

<400> SEQUENCE: 9

Cys Leu Leu Leu Asp Ile Val Ala Pro Lys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: overlapping peptide sequence

<400> SEQUENCE: 10

Ile Val Ala Pro Lys Leu Arg Pro Val
1               5

<210> SEQ ID NO 11
<211> LENGTH: 9
<212> TYPE: PRT
<213> ORGANISM: Homo sapiens

<400> SEQUENCE: 11

Ser Pro Met Ile Val Gly Ser Pro Arg
1               5

<210> SEQ ID NO 12
<211> LENGTH: 10
<212> TYPE: PRT

```
<213> ORGANISM: Artificial Sequence
<220> FEATURE:
<223> OTHER INFORMATION: overlapping peptide sequence

<400> SEQUENCE: 12

Ser Pro Met Ile Val Gly Ser Pro Trp Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: overlapping peptide sequence

<400> SEQUENCE: 13

Ser Pro Met Ile Val Gly Ser Pro Trp Ala Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: overlapping peptide sequence

<400> SEQUENCE: 14

Ser Pro Trp Ala Leu Thr Gln Pro Leu Gly Leu
1               5                   10

<210> SEQ ID NO 15
<211> LENGTH: 9
<212> TYPE: PRT
<213> ORGANISM: Artificial Sequence
<220> FEATURE:
<223> OTHER INFORMATION: overlapping peptide sequence

<400> SEQUENCE: 15

Ser Pro Trp Ala Leu Thr Gln Pro Leu
1               5
```